United States Patent [19]
Lander

[11] Patent Number: 5,827,195
[45] Date of Patent: Oct. 27, 1998

[54] ELECTROCARDIOGRAM NOISE REDUCTION USING MULTI-DIMENSIONAL FILTERING

[75] Inventor: Paul Lander, Lincoln, Mass.

[73] Assignee: Cambridge Heart, Inc., Bedford, Mass.

[21] Appl. No.: 853,914

[22] Filed: May 9, 1997

[51] Int. Cl.$^6$ .......................... A61B 5/0402; A61B 5/0452
[52] U.S. Cl. ............................ 600/509; 600/516; 600/517
[58] Field of Search .................................... 600/509, 516, 600/517

[56] References Cited

U.S. PATENT DOCUMENTS

| | | |
|---|---|---|
| 4,082,087 | 4/1978 | Howson . |
| 4,084,583 | 4/1978 | Hjort . |
| 4,422,459 | 12/1983 | Simson . |
| 4,458,691 | 7/1984 | Netravali . |
| 4,458,692 | 7/1984 | Simson . |
| 4,492,235 | 1/1985 | Sitrick . |
| 4,556,962 | 12/1985 | Widrow et al. . |
| 4,622,980 | 11/1986 | Kunig . |
| 4,630,204 | 12/1986 | Mortara . |
| 4,732,157 | 3/1988 | Kaplan et al. . |
| 4,751,931 | 6/1988 | Briller et al. . |
| 4,760,540 | 7/1988 | Yuen . |
| 4,781,201 | 11/1988 | Wright et al. . |
| 4,783,660 | 11/1988 | Pierce . |
| 4,793,361 | 12/1988 | DuFault . |
| 4,802,491 | 2/1989 | Cohen et al. . |
| 4,807,173 | 2/1989 | Sommen et al. . |
| 4,917,099 | 4/1990 | Stice . |
| 4,974,598 | 12/1990 | John . |
| 4,979,110 | 12/1990 | Albrecht et al. . |
| 4,993,423 | 2/1991 | Stice . |
| 5,010,888 | 4/1991 | Jadvar et al. . |
| 5,020,540 | 6/1991 | Chamoun . |
| 5,020,541 | 6/1991 | Marriott . |

(List continued on next page.)

OTHER PUBLICATIONS

Adam et al., "Ventricular Fibrillation and Fluctuations in the Magnitude of the Repolarization Vector," Computers in Cardiology, pp. 241–244 (1982).

Adam et al., "Fluctuations in T–Wave Morphology and Susceptibility to Ventricular Fibrillation," J. Electrocardiology 17(3), pp. 209–218 (1984).

Adam et al., "Estimation of Ventricular Vulnerability to Fibrillation Through T–Wave Time Series Analysis," Computers in Cardiology, pp. 307–310 (1981).

Atarius et al., "Signal–to–Noise Ratio Enhancement of Cardiac Late Potentials Using Ensemble Correlation.", IEEE Trans. Biomed. Engr., vol. 42(11) (1995), pp.1132–1137.

Baraniuk et al., "A Signal–Dependent Time–Frequency Representation: Optimal Kernel Design.", IEEE Trans. on Signal Proc., vol. 41, No. 4 (1993), pp.1589–1602.

Cano et al., "Enhancement of Low–Level ECG Components in Noise With Time–Sequenced Adaptive Filtering," J. Electrocardiology, vol. 23 Supplement, pp. 176–183 (1990).

Cano et al., "Enhancement of Surface HIS Activity With Adaptive Filtering", Proc. IEEE Eng. in Med. & Biol. Soc. II (1) (1989), pp. 22–23.

Changxiu et al., "A New Algorithm for Adaptive Noise Cancellation Using Singular Value Decomposition," Acta Automatica Sinica, vol. 12, No. 2, pp. 146–153 (Apr. 1986) (Engl. tranlation and original paper).

(List continued on next page.)

*Primary Examiner*—William E. Kamm
*Assistant Examiner*—Carl H. Layno
*Attorney, Agent, or Firm*—Fish & Richardson P.C.

[57] ABSTRACT

Noise is reduced from a received ECG signal representative of activity of the heart of a patient. A collection of beats from the ECG signal is selected and transformed into a multi-dimensional representation. A multi-dimensional filter function is applied to the multi-dimensional representation to enhance a signal-to-noise ratio of the collection of beats.

37 Claims, 15 Drawing Sheets

U.S. PATENT DOCUMENTS

| | | |
|---|---|---|
| 5,046,504 | 9/1991 | Albert et al. . |
| 5,054,496 | 10/1991 | Wen et al. . |
| 5,107,849 | 4/1992 | Bellin et al. . |
| 5,109,862 | 5/1992 | Kelen et al. ............................ 600/515 |
| 5,146,926 | 9/1992 | Cohen . |
| 5,148,812 | 9/1992 | Verrier et al. ........................... 600/517 |
| 5,188,116 | 2/1993 | Pommrehn et al. . |
| 5,234,404 | 8/1993 | Tuttle et al. . |
| 5,237,995 | 8/1993 | Cano . |
| 5,265,617 | 11/1993 | Verrier et al. . |
| 5,318,037 | 6/1994 | Evans et al. . |
| 5,323,783 | 6/1994 | Henkin et al. . |
| 5,341,811 | 8/1994 | Cano . |
| 5,348,020 | 9/1994 | Hutson . |
| 5,377,687 | 1/1995 | Evans et al. . |
| 5,419,337 | 5/1995 | Dempsey et al. . |
| 5,421,342 | 6/1995 | Mortara . |
| 5,437,285 | 8/1995 | Verrier et al. . |
| 5,469,857 | 11/1995 | Laurent et al. . |
| 5,520,191 | 5/1996 | Karlsson et al. . |
| 5,520,683 | 5/1996 | Subramaniam et al. . |
| 5,560,370 | 10/1996 | Verrier et al. . |
| 5,564,428 | 10/1996 | Soernmo et al. . |
| 5,570,696 | 11/1996 | Arnold et al. . |

OTHER PUBLICATIONS

Cohen, "Time–Frequency Distributions—A Review", Proc. IEEE, vol. 77 (1989), pp. 941–981.

Damen et al., "The Use of the Singular Value Decomposition in Electrocardiology," Medical & Biological Engineering & Computing, pp. 473–482 (1982).

de Weerd, "A Posteriori Time–Varying Filtering of Averaged Evoked Potentials. 1. Introduction and Conceptual Basis.", Biol. Cybern., vol. 41 (1981), pp. 211–222.

de Weerd et al., "A Posteriori Time–Varying Filtering of Averaged Evoked Potentials. II. Mathematical and Computational Aspects.", Biol. Cybern., vol. 41 (1981), pp. 223–234.

de Weerd, "Facts and Fancies About a posteriori Wiener Filtering", IEEE Trans. Biomed. Eng., vol. 28 (1981), pp. 252–257.

de Weerd et al., "Spectro–Temporal Representation and Time–Varying Spectra of Evoked Potentials.", Biol. Cybern., vol. 41 (1981), pp. 101–117.

de Weerd et al., "Theory and Practice of a posteriori Wiener Filtering of Averaged Evoked Ptentials", Biol. Cybern., vol. 30 (1978), pp. 81–94.

Dimri, "On the Time–Varying Wiener filter", Geophys. Prospecting, vol. 34 (1986), pp. 904–912.

Doyle, "A Proposed Methodology for Evaluation of the Wiener Filtering Method of Evoked Potential Estimation", Electroencephalogr. Clin. Neurophysiol., vol. 43 (1977), pp. 749–751.

El–Sherif et al., "Beat–to–Beat High–Resolution Electrocardiogram; Technical and Clinical Aspects," Progress in Cardiovascular Diseases, vol. XXXV, No. 6, pp. 407–415 (1993).

El–Sherif et al., "Appraisal of a Low Noise Electrocardiogram," J. Am. Coll. Cardiol. 1(2), pp. 456–467 (1983).

Evans et al., "Redundancy Reduction for Improved Display and Analysis of Body Surface Potential Maps," Circulation Research, vol. 49, No. 1, pp. 197–203 (1981).

Ferrara et al., "The Time–Sequenced Adaptive Filter", IEEE Trans. Acoust., Speech and Sig. Proc., vol. 29 (1981), pp. 679–683.

Gabor, "Theory of Communication", J. IEE, vol. 93 (1946), pp. 429–457.

Haberl et al., "Top–Resolution Frequency Analysis of Electrocardiogram With Adaptive Frequency Determination", Circulation, vol. 82 (1990), pp. 1183–1192.

Hlawatsch et al., "Linear and Quadratic Time–Frequency Signal Representations", IEEE Sig. Proc. Mag., vol. 9 (1992), pp. 21–67.

Jones et al., "A Resolution Comparison of Several Time–Frequency Representations", IEEE Trans. Sig. Proc., vol. 40 (1992), pp. 413–420.

Kaufer et al., "Optimization of Multi–Ring Sensing Electrode Set," Annual International Conference of the IEEE Engineering in Medicine and Biology Society, vol. 12, No. 2, pp. 0612–0613 (1990).

Kelen, "Spectral Turbulence Analysis of the Signal–Averaged Electrocardiogram Its Predictive Accuracy for Inducible Sustained Monomorphic Ventricular Tachycardia", Am. J. Cardiol., vol. 67 (1991), pp. 965–975.

Lander et al., "Advanced Digital Techniques for the Recovery of Cardiac Micropotentials", Proceedings of Computers in Cardiol., IEEE Computer Society Press (1993), pp. 193–196.

Lander et al., "The Analysis of Ventricular Late Potentials Using Orthogonal Recordings", IEEE Trans. Biomed. Engr., vol. 35 (1988), pp. 629–639.

Lander et al., "Optimal Filtering and Quality Control of the Signal–Averaged ECG: High–Fidelity 1–Minute Recordings", Circulation, vol. 91 (1995), pp. 1495–1505.

Lander et al., "Performance Assessment of Optimal Filtering of the High Resolution Electrocardiogram", In: Computers in Cardiology, IEEE Computer Society Press, Los Alamitos, CA (1994), pp. 693–695.

Lander et al., "Principles and Signal Processing Techniques of the High–Resolution Electrocardiogram," Prog. Cardiovasc. Dis. vol. 35(3) (1992), pp. 169–188.

Lander et al., "Spectro–Temporal Analysis of Ventricular Late Potentials", J. Electrocardiol., vol. 23 (1990), pp. 95–108.

Lander et al., "Spectro–Temporal Mapping: The Next Generation in Late Potential Analysis.", J. Am. Coll. Cardiol., II:199A (1988).

Meyer et al., "Electrocardiogram Baseline Noise Estimation and Removal Using Cubic Splines and State–Space Computation Techniques," Computers and Biomedical Research 10, pp. 459–470 (1977).

Mortara, "Source Consistency Filtering—Application to Resting ECGs," J. Electrocardiology, vol. 25 Supplement, pp. 200–206 (1992).

Mortara, "Source Consistency Filtering—A New Tool for ECG Noise Reduction," IEEE, pp. 125–128 (1992).

Nearing et al., "Dynamic Tracking of Cardiac Vulnerability by Complex Demodulation of the T Wave," Science, vol. 252, pp. 437–440 (1991).

Nearing et al., "Personal Computer System for Tracking Cardiac Vulnerability by Complex Demodulation of the T Wave," J. Appl. Physiol. 74, pp. 2606–2612 (1993).

Pedretti et al., "Prediction of Late Arrhythmic Events After Acute Myocardial Infarction . . . Sustained Monomorphic Ventricular Tachycardia," A. J. Cardiol., vol. 71, No. 13, pp. 1131–1141 (1993).

Rasquinha et al., "Directional Depolarization Sensors of Body Surface ECG," Annual International Conference of the IEEE Engineering in Medicine and Biology Society, vol. 13, No. 4, pp. 1680–1681 (1991).

Ring et al., "Exercise–Induced ST Segment Alternans," American Heart Journal, vol. 111, No. 5, pp. 1009–1011 (1986).

Rosenbaum et al., "Electrical Alternans and Vulnerability to Ventricular Arrhythmias," New England Journal of Medicine 330, pp. 235–241 (1994).

Salerno et al., "Ventricular Arrhythmias During Acute Myocardial Ischaemia in Man. The Role and Significance of R–St–T Alternans . . . ," European Heart Journal 7 (Supp. A), pp. 63–75 (1986).

Shvartsman et al., "Multichannel Signal Processing Based on Logic Averaging," IEEE Transactions on Biomedical Engineering, vol. BME–29, No. 7, pp. 531–536 (1982).

Smith et al., "Electrical Alternans and Cardiac Electrical Instability," Circulation, vol. 77, No. 1, 110–121 (1988).

Smith et al., "Subtle Alternating Electrocardiographic Morphology as an Indicator of Decreased Cardiac Electrical Stability," Computers in Cardiology, pp. 109–112 (1985).

Smith, "The Stochastic Nature of Cardiac Electrical Instability: Theory and Experiment," thesis, Mass. Institute of Technology (1985).

Strackee et al., "Some Statistical Aspects of Digital Wiener Filtering and Detection of Prescribed Frequency Components in Time Averaging of Biological Studies", Biol. Cybern., vol. 28 (1977), pp. 55–61.

Verrier et al., "Electrophysiologic Basis for T Wave Alternans as an Index of Vulnerability to Ventricular Fibrillation," J. Cardiovascular Electrophysiology, vol., 5, No. 5, pp. 445–461 (1994).

Walter, "A posteriori Wiener Filtering of Averaged Evoked Responses", Electroencephalogr. Clin. Neurophysiol. Suppl. 27 (1969), pp. 61–70.

Wel et al., "A New Method for Reducing Signal–Overlapping Noise in Standard Electrocardiogram," Proceedings of Computers in Cardiology, pp. 795–797 (1993).

Widrow, "Adaptive Interference Canceling," Adaptive Signal Processing, Applications Part IV, Chap. 12, Prentice–Hall, Englewood Cliffs, NJ, pp. 302–367 (1985).

Zareba et al., "T Wave Alternans," J. Am. Coll. Cardiol., vol. 23, pp. 1541–1546 (1994).

Zimmerman et al., "Beat–to–Beat Detection of Ventricular Late Potentials with High–Resolution Electrocardiography," American Heart Journal, vol. 121, No. 2, Part 1, pp. 576–585 (1991).

P. Lander et al., "Principles and signal processing techniques of the high–resolution electrocardiogram," Progress in Cardiovascular Disease 35:169–188 (1982).

P. Lander et al., "Spectro–temporal analysis of ventricular late potentials", Journal of Electrocardiology 23:95–108, (1990).

ELECTROCARDIOGRAM NOISE REDUCTION USING MULTI-DIMENSIONAL FILTERING

BACKGROUND

The invention relates to reducing noise in an electrocardiogram.

Electrical activity of the heart generates an electrical potential on the body surface. At any given location on the body, this potential includes contributions from every region of the heart, with the contribution from a particular region being inversely proportional to the square of the distance from the region to the location on the body. Given the anatomy of the heart and chest, the potentials at most locations on the body surface represent summed electrical activity from a large region of the heart.

The body surface electrocardiogram ("ECG") is a measure of electrical activity of the heart. The ECG provides a measure of the potential difference between two points on the body surface as a continuous function of time. The ECG is routinely measured using standard ECG electrodes. Commonly, ten electrodes are used, four of which are near the limbs and six of which span the chest, primarily on the left side. The signals recorded from these electrodes are processed to form a standard set of twelve ECG leads.

Each of the standard twelve ECG leads represents the difference between two electrical potentials that are located a significant distance from one another. Standard leads I, II and III represent the difference between pairs of the limb electrodes. They are referred to as bipolar leads because they represent the difference between two electrodes. Standard leads AVR, AVL, AVF and V1–V6 represent the difference between an electrode and Wilson's central terminal, a reference created by averaging three of the limb electrodes. Leads referenced to Wilson's central terminal are referred to as unipolar leads.

SUMMARY

The invention provides techniques for enhancing the signal-to-noise ratio of low-level signals in an ECG. There are many situations in which it is desirable to enhance the signal-to-noise ratio of the ECG for its analysis and interpretation. This is true both for single ECG beats and in computing representative beats from an ensemble of ECG beats. Sample applications include, but are not limited to, the twelve-lead electrocardiogram, vectorcardiography, ambulatory monitoring, measurement of T wave altemans, detection of myocardial ischemia, and physiologic stress testing.

In one aspect, generally, the invention features reducing noise from an ECG signal representative of activity of the heart of a patient. After a physiologic condition of the patient is altered using non-surgical techniques to stress the heart of the patient, an ECG signal representative of activity of the heart and including a sequence of beats is received. A collection of beats is selected from the ECG signal and transformed into a multi-dimensional representation. Next, a multi-dimensional filter function is applied to the multi-dimensional representation to enhance a signal-to-noise ratio of the collection of beats.

Embodiments of the invention may include one or more of the following features. The physiologic condition of the patient may be altered by instructing the patient to engage in normal physical activity for an extended period, and the ECG signal may be recorded using an ambulatory monitor. The physiologic condition of the patient also may be altered by subjecting the patient to physiologic stress testing.

A collection of beats that occupy a particular time epoch may be selected. As an alternative, the selected collection of beats may be characterized by ECG shape, wave components, or wave timing, or by a particular contextual relationship to irregular beats. A collection of beats also may be selected based on patterns of beat-to-beat variation, such as alternating components or N-geminy components.

The multi-dimensional representation may be a two-dimensional representation. For example, transformation of the collection of beats into a multi-dimensional representation may include application of a wavelet transform to obtain a two-dimensional, time-scale representation of the collection of beats. As an alternative, the transformation may include using a numerical basis set derived from an electrocardiogram signal to obtain the two-dimensional representation, or using a Wigner-Ville distribution to obtain a quadratic two-dimensional representation.

The multi-dimensional representation may be enhanced to reduce variance and interference terms by convolution with a multi-dimensional function, such as a two-dimensional Gaussian function, a time-frequency kernel derived from an electrocardiogram signal, or an adaptive, signal-dependent kernel.

Generation of the filter may include incorporating beats from the collection of beats being processed in an a posteriori computation of an optimally-filtered signal estimate. A posteriori information is any information gained from analysis or measurement of the collection of ECG beats used to create the filter. An example is the a signal-dependent kernel obtained directly from the collection of ECG beats. Generation of the filter also may include incorporation of a priori information about the ECG, such as information derived from beats which are not part of the collection being processed, or information derived from sources other than the ECG being processed. A priori information is any information that is not obtained from the collection of beats, and may include, for example, the use of a time-frequency kernel derived from another electrocardiogram signal, or from a dictionary of previously-compiled electrocardiogram signals.

Application of the filter may include performing an inverse transformation of the multi-dimensional representation after filtering to obtain a one-dimensional signal estimate. The inverse transformation may include an inverse wavelet transform or an inverse Wigner-Ville transformation.

A measure of alternans or a localized EEG may be generated from the enhanced collection of beats. In general, a localized ECG signal reflects a difference between the ECG signals produced by two or more closely-positioned electrodes. As an alternative, a localized ECG signal may be generated from the received ECG signal, and the collection of beats may be selected from the localized ECG signal. An average of the collection of beats may be calculated and transformed into a two-dimensional representation.

In another aspect, generally, the invention features measuring alternans in an ECG signal. A collection of beats is selected from a received ECG signal representative of activity of a heart of a patient, and is transformed into a multidimensional representation. A multi-dimensional filter function is applied to the multi-dimensional representation to enhance a signal-to-noise ratio of the collection of beats. A measure of alternans then is generated from the enhanced collection of beats.

In another aspect, generally, the invention features generating a localized ECG signal. A collection of beats is selected from a received ECG signal representative of activity of a heart of a patient, and is transformed into a multi-dimensional representation. A multi-dimensional filter function is applied to the multi-dimensional representation of the collection of beats to enhance a signal-to-noise ratio of the collection of beats. A localized ECG signal then is generated from the enhanced collection of beats.

In another aspect, generally, the invention features generating a collection of localized beats. A localized ECG signal is generated from a received ECG signal representative of activity of a heart of a patient. Thereafter, a collection of localized beats is selected from the localized ECG signal and transformed into a multi-dimensional representation. A multi-dimensional filter function is applied to the multidimensional representation to enhance a signal-to-noise ratio of the collection of localized beats.

In another aspect, generally, the invention features evaluating an interval of an ECG signal to, for example, measure QT dispersion in the ECG signal. Corresponding collections of beats are selected from several leads of a received ECG signal representative of activity of a heart of a patient, and are transformed into multi-dimensional representations. A multi-dimensional filter function is applied to the multi-dimensional representations of the collections of beats to enhance signal-to-noise ratios of the collections of beats. The QT interval then is measured for each enhanced collection of beats. The QT intervals for the different leads then are compared to generate a measure of QT dispersion.

The techniques of the invention employ a multi-dimensional filter, such as a two-dimensional, time-frequency-plane-Wiener ("TFPW") filter, that is useful when there are noise levels that can mask signal information in the electrocardiogram, such as may occur when signals of interest have small values (e.g., the signals of interest are microvolt-level potentials).

The Wiener theory of filtering may be stated generally as:

$$h(\tau) = \frac{\rho_{xy}(\tau)}{\rho_{xx}(\tau)},$$

where $h(\tau)$ is the Wiener filter, $\rho_{xy}(\tau)$ is the correlation between the filter output and input, and $\rho_{xx}(\tau)$ is the autocorrelation of the filter's input. The general Wiener theory presupposes that the second order statistics of the signal and noise are known a priori and are sufficient to characterize the signal and noise processes. This is rarely the case in real-world applications, such as in analysis of the ECG.

Noise originates from muscle, nervous system activity, and movement. Small ECG signals, such as T-wave alternans, ventricular late potentials and ST segment changes, may be masked in higher levels of noise. The efficient and effective noise reduction techniques provided by the invention promise to be of major benefit in electrocardiography, particularly in physiologic stress testing and ambulatory monitoring.

Ensemble averaging has been employed to reduce noise in the electrocardiogram. With averaging, noise in the RMS amplitude is reduced by an expected factor of the square root of R, where R is the number of beats averaged. The TFPW filter accelerates noise reduction relative to ensemble averaging, requires a smaller number of beats to reach a particular noise endpoint, and can be used to characterize dynamic or time-varying ECG activity.

The TFPW filter transforms an ECG signal into a two-dimensional representation that is based on a decomposition of the ECG signal with regard to the time-frequency structure of the ECG signal. The ECG signal is interpreted, and varies primarily, within the time domain. However, different time periods have differing frequency content. For example, the ST segment waveform is mostly low frequency (less than 30 Hz) while the QRS complex occupies a wider bandwidth (typically 10–250 Hz). Noise is nonstationary in time but has a Gaussian distribution across an ensemble of ECG beats. These time-frequency variations of signal and noise can be separated by averaging collections of beats and producing two-dimensional representations of individual beats and associated average beats. In the TFPW filter process, the two-dimensional representations may be enhanced using two-dimensional smoothing. The technique permits matching of the smoothing to the ECG under study to remove uncertainties and non-signal terms in the two-dimensional representations. The smoothing may include a two-dimensional Gaussian function, a signal-dependent ECG kernel, or a transformation basis set built from ECG waveforms.

The TFPW filter is based on a posteriori Wiener filtering methodology and is a departure from previous one-dimensional signal-to-noise ratio enhancing filters in that the TFPW filter accommodates nonstationary aspects of the ECG signals. The TFPW filter may be applied in any situation in which an improvement in signal-to-noise ratio would be desirable. An important application is during physiologic stress testing. With an exercising patient, noise levels in the ECG may be too high to detect small signals such as electrical alternans, subclinical ST segment changes, ventricular late potentials, and subtle changes in the T wave and QRS complex. As these signals change during stress, it would be useful to measure their dynamic or time-varying character. Monitoring, particularly in ambulatory patients, is another application of the TFPW filter. High noise levels are common in ambulatory recordings and usually preclude the analysis of small, limited-duration signals.

Another important application of the TFPW filter is in identification of acute myocardial infarction. Changes in impulse conduction and the state of myocardial tissue during an evolving acute myocardial infarction are likely to cause subtle changes in the ECG waveform. The TFPW filter allows a series of sequential ECG recordings to be made to identify these changes and chart their evolution.

The subject's heart may be stressed through exercise stress testing using, for example, an ergometer or a treadmill. As an alternative, the subject's heart may be stressed using pharmacological agents.

Stress testing presents significant challenges to measuring localized electrocardiograms. Cardiac stress testing is perhaps the most important and common test in cardiology, being performed more than eight million times a year in the United States alone. Cardiac stress testing is widely used as the primary assessment of whether coronary artery disease is altering the function of the heart. The test in its present form has serious limitations. According to some analyses, traditional stress testing is able to detect typically only six out of every ten patients with coronary artery disease and falsely detects typically three out of every ten patients without significant coronary artery disease. The standard cardiac stress test therefore appears to suffer from limited sensitivity. Improvement of cardiac stress testing is made difficult by the demanding conditions under which the test is performed. Exercise results in noise due to electrical activity of chest muscles and movement artifacts at the electrodes. These factors severely impede precise measurement of the ECG, particularly where microvolt-level potentials of interest are masked by noise and movement artifact.

Other features and advantages of the invention will become apparent from the following description, including the drawings, and from the claims.

DESCRIPTION

Figure 1:
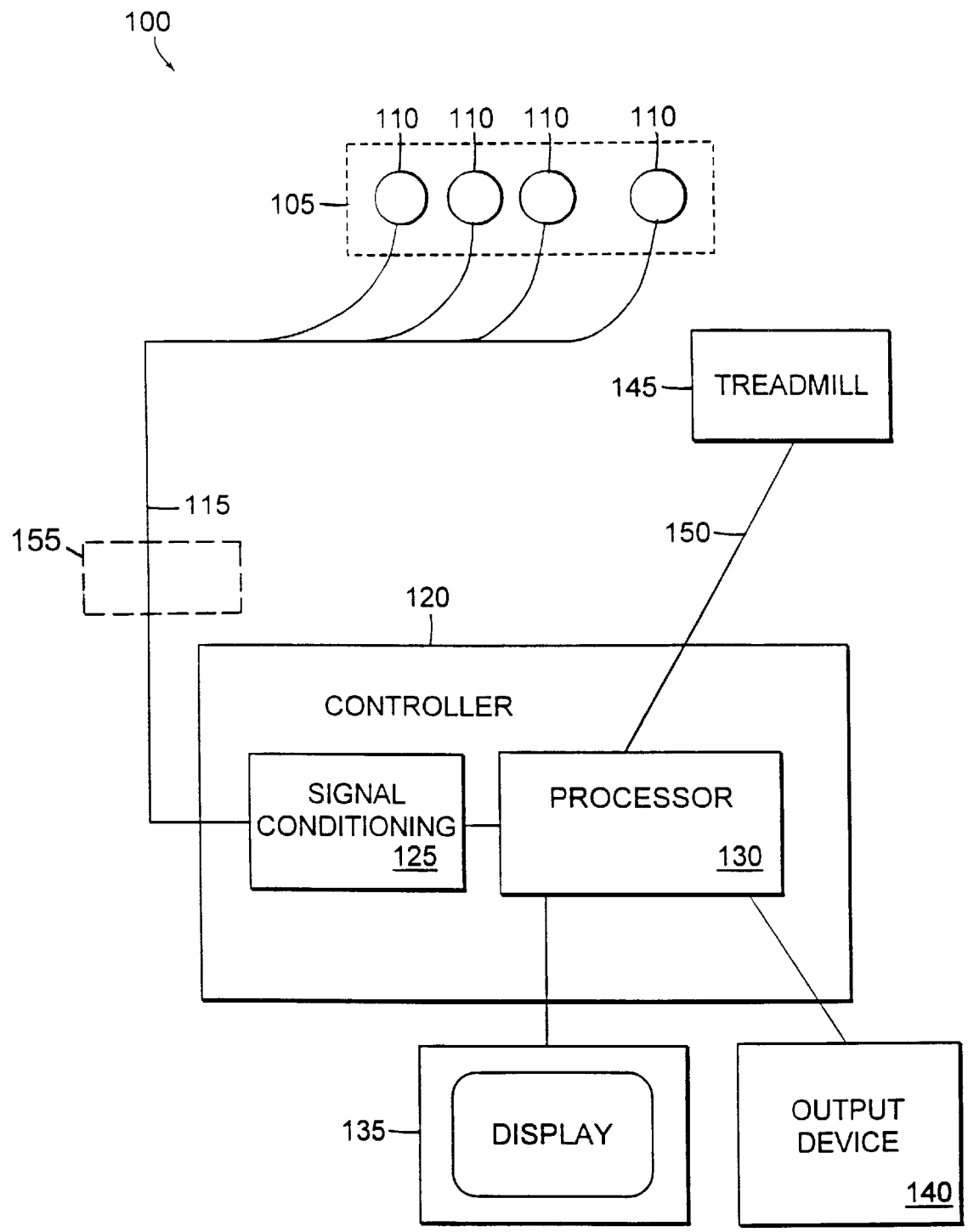
FIG. 1 is a block diagram of an ECG system.

Referring to FIG. 1, a ECG system 100 that may be used during physiologic stressing of a patient's heart includes a set 105 of electrodes 110. The electrodes may be standard ECG electrodes, or may be an array of electrodes applied to cover the anterior, lateral and posterior areas of the torso. The electrodes function separately from one another, but may be physically affixed together to form a flexible band or other arrangement. The system 100 further includes a set of leads 115 that connect the electrodes to a system controller 120. The controller includes signal conditioning circuitry 125 and a processor 130. The circuitry 125 receives analog signals from the leads 115 and provides conditioned digital signals to the processor 130. The processor 130 processes the conditioned signals to produce results that the processor then provides to a connected display 135 or to an output device 140, such as a printer. The processor may optionally control physiologic stress of the patient's heart by controlling an exercise device, such as a treadmill 145 having programmable slope and walking speed, through control signals supplied through a cable 150. Similarly, an optional recording device 155 of an ambulatory system may be used to record signals from the leads for an extended period of time (e.g., 24 hours). The recording device 155 then is connected to the controller 120 to permit the controller 120 to process the recorded data.

Figure 2:
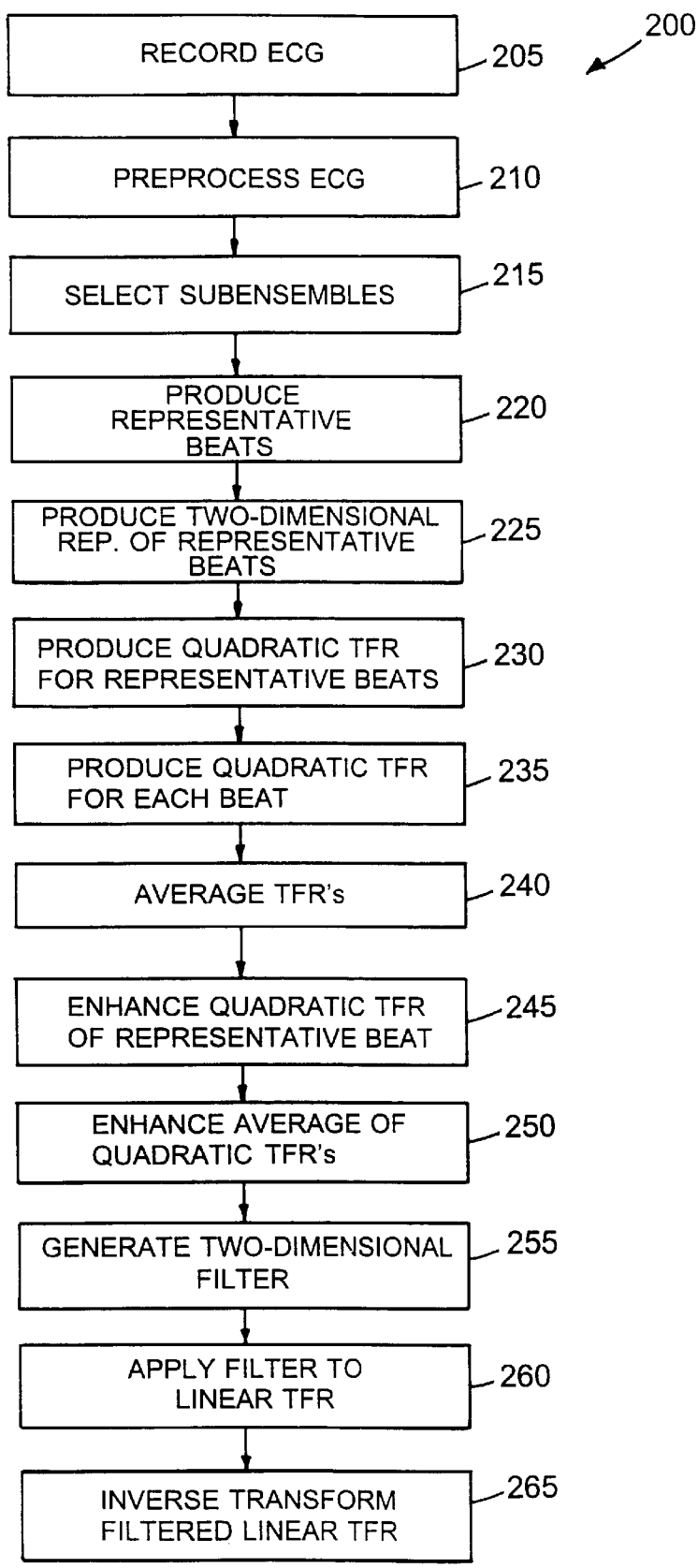
FIG. 2 is a flowchart of a procedure for processing ECG signals.

Referring to FIG. 2, the controller 120 processes ECG data according to a procedure 200 to produce ECG beats having enhanced signal-to-noise ratios. Initially, the controller 120 records a continuous ECG from the body surface using the electrodes 110 (step 205). The recorded ECG, which also may be referred to as an ensemble of beats, may be recorded, for example, during a physiologic stress test that includes a rest period, stages of increasing stress, and a recovery period. This type of ECG may be analyzed to detect alternans or myocardial ischemia due to coronary artery disease.

The recorded ECG also may correspond to a resting ECG recorded from a supine patient. A resting ECG may be recorded routinely or in an emergency room when an acute myocardial infarction is suspected. Similarly, the recorded ECG may be produced using a bedside monitor in a hospital. This may be done, for example, after a revascularization procedure, such as balloon angioplasty to open a previously occluded artery, in which case analysis of the ECG may identify reocclusion of the artery.

The recorded ECG also may be produced using an ambulatory recorder to, for example, assess transient myocardial ischemia. Typically, an ECG produced using an ambulatory recorder will include twenty four hours or more of ECG data.

In one implementation, ECG data are acquired at a sampling rate of at least 250 Hz, a bandwidth from at least 0.05 to 100 Hz, and an amplitude quantization step of not more than 15 $\mu V$ for the least significant bit of digital data. The recorded ECG data are formed into an ensemble of aligned ECG beats that are held in an array for subsequent processing.

Figure 3:
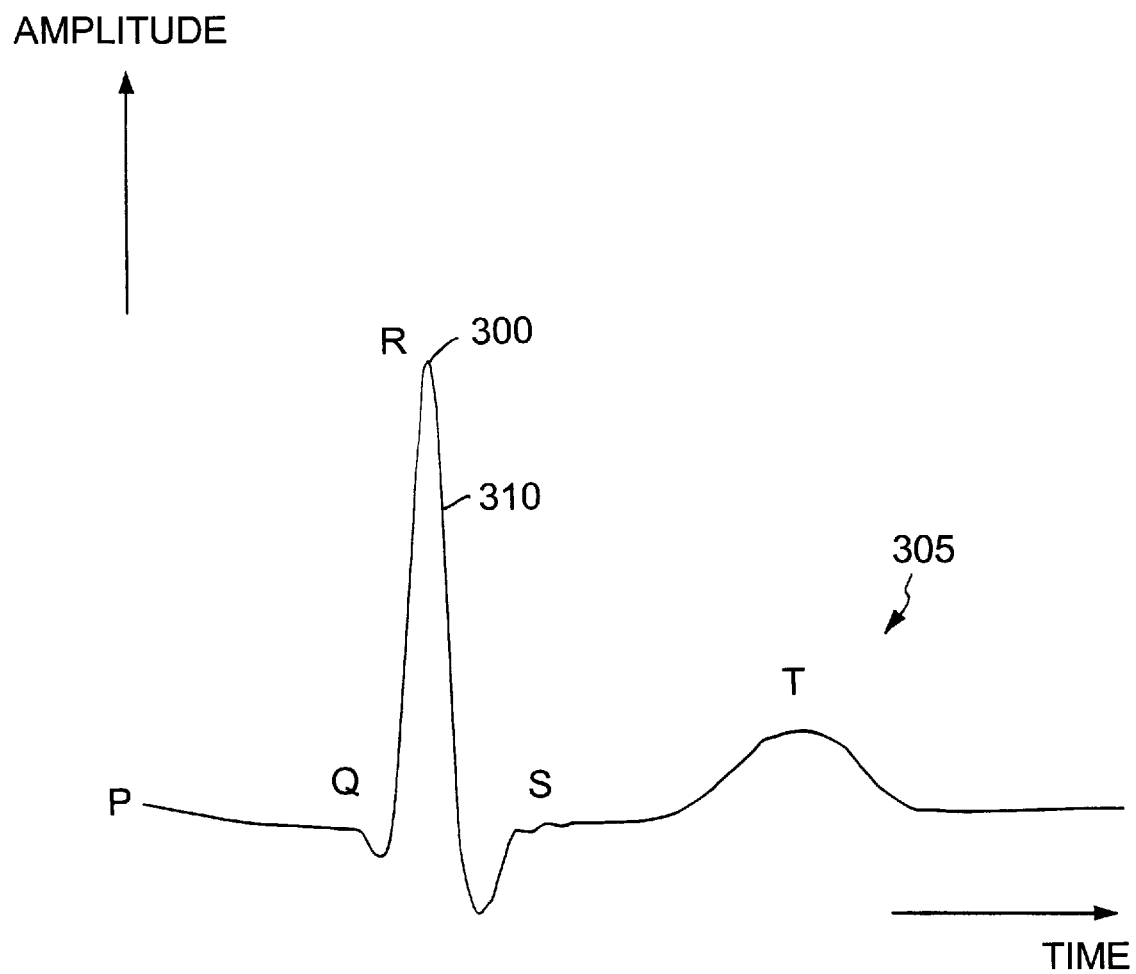
FIG. 3 is a schematic representation of an ECG waveform.

Beats are preliminarily detected using an R wave trigger. Referring to FIG. 3, the R wave 300 of an ECG beat 305 includes the point of maximum amplitude. The QRS complex 310 of the beat, which corresponds to ventricular contraction, is compared with a template beat that may be selected either manually by the user or automatically by the controller 120. Typically, cross-correlation is used to time-align each beat with a similar point within the QRS complex of the template beat. See P. Lander et al., "Principles and signal processing techniques of the high-resolution electrocardiogram," Prog. Cardiovasc. Dis. 35:169–188 (1992), which is incorporated by reference.

Referring again to FIG. 2, once the ensemble of ECG beats is recorded, the ECG signal is preprocessed (step 210). For example, each beat in the ensemble may be DC adjusted by subtracting the zero ECG value from each data sample in the beat. The zero ECG value, which is the value of the ECG when there is no cardiac electrical activity, may be approximated by taking the value of the ECG at the QRS onset, or a value within the TP interval. Subtracting the zero ECG value removes the effect of constant or slowly varying potentials of non-cardiac origin. Similar results may be achieved by applying a digital highpass filter to the ECG to remove low frequency components, or slow waves, of the ECG, such as the ST segment waveform. Highpass filtering may be useful in estimating short-time, high frequency components of the ECG, such as ventricular late potentials.

Preprocessing also may include the exclusion of excessively noisy beats from the ensemble. ECG noise is typically nonstationary, both locally (within an individual beat) and globally (within the ensemble). By assuming that ensemble noise follows a Gaussian distribution, outliers of this distribution may be used to identify particularly noisy beats. In particular, a measure of the variance, or noise power, of the ensemble may be used to exclude noisy beats. The variance (VAR) of an ensemble of R beats may be expressed as:

$$\text{VAR}[\bar{x}_R(t)] = \left\{ \sum_{i=1}^{R} x_i^2(t)/R - \left( \sum_{i=1}^{R} x_i(t)/R \right)^2 \right\} /R,$$

assuming that noise is uncorrelated from beat to beat. The measurement of the variance may be made in a window of 50–100 ms duration in the ST segment. The variance of a new beat ($X_{R+1}$) may be estimated from the variances for ensembles of R+1 beats and R beats as:

$$\text{VAR}[\bar{x}_{R+1}(t)] = R \left\{ \text{VAR}[\bar{x}_{R+1}(t)] \cdot \left( \frac{R+1}{R} \right) - \text{VAR}[\bar{x}_R(t)] \right\}.$$

This expression may be used to measure the variance of each new beat as the new beat becomes available. Empirical analysis has shown that approximately sixteen ECG beats are initially needed to achieve a numerically stable estimate of individual beat noise. As an alternative, the variance of each beat may be calculated by excluding the beat from the ensemble variance calculation. After the variances of the beats are determined, the beats are ranked by variance and the noisiest beats are removed from the ensemble.

Next, the controller 120 selects collections, or subensembles, of beats from the recorded and preprocessed ECG (step 215). Examples of subensembles may include: stages of a stress test; regular intervals (e.g., five to fifteen minute intervals in an emergency room); and periods of the day in, for example, ambulatory or hospital monitoring. Similarly, subensembles may be selected based on levels of physiologic activity associated with recorded data.

Figure 3A:
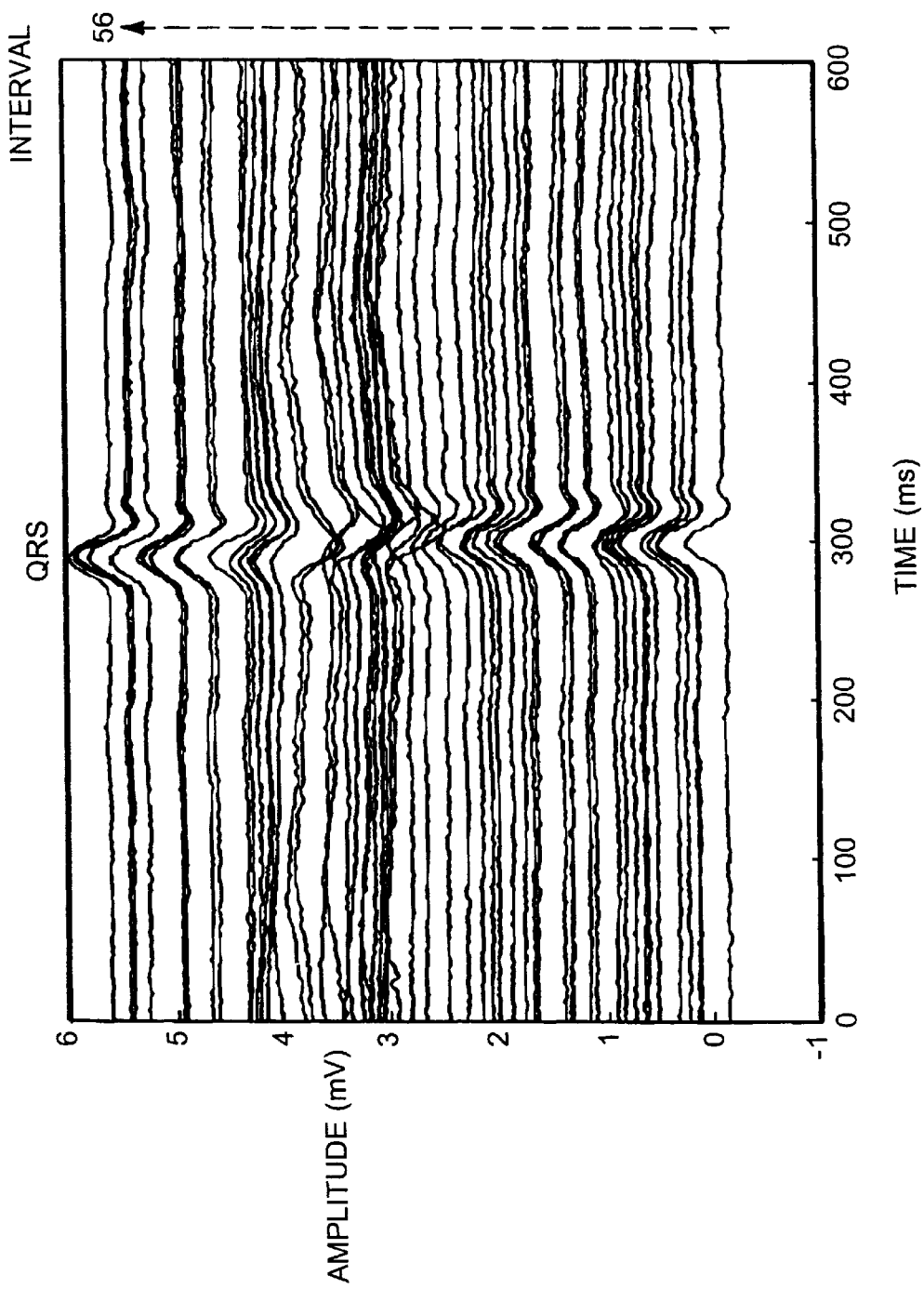
FIGS. 3A–3D are schematic representations of collections of ECG waveforms.

The subensembles also may be selected to include beats characterized by shape, components, or timing. For example, collections of beats may be chosen based on periods in which the ECG components (e.g., the QRS complex) have uniform shapes. The ECG may change in shape during exercise. FIG. 3A shows representative beats (i.e., average beats) computed for sequential thirty second intervals during a twenty eight minute stress test. The first interval is during the control, or rest, period. Exercise begins at the eighth interval, and the level of exercise is increased progressively. Recovery (i.e., the cessation of exercise and adoption of a stationary, standing position) begins at the forty-eighth interval. FIG. 3A shows how the QRS complex of the ECG changes shape during exercise. At approximately interval number thirty two, the QRS complex changes from an upright shape to a biphasic deflection.

Figure 3B:
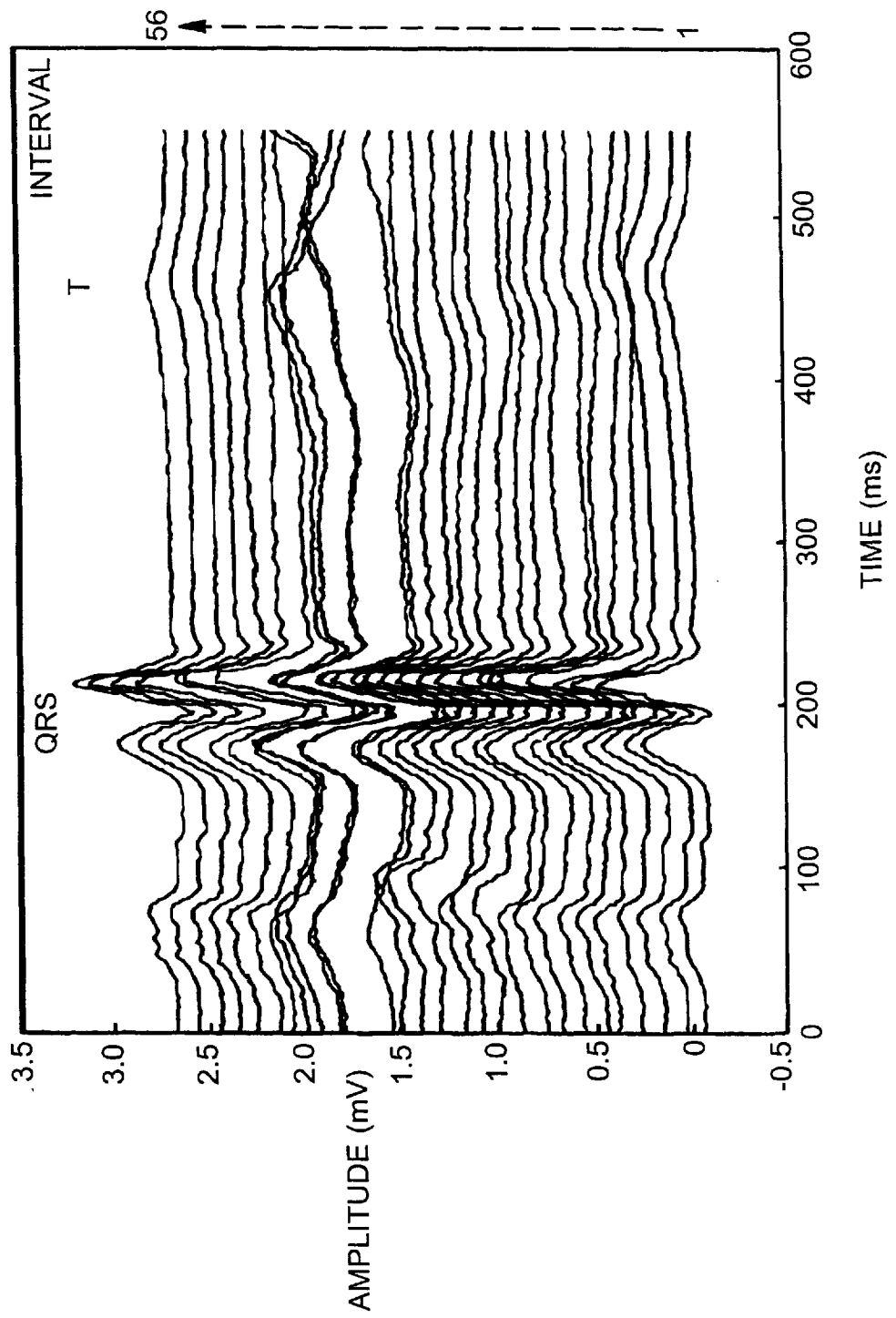

Similarly, FIG. 3B shows changing morphology for the T wave. The T wave inverts at the onset of stress (i.e., at the ninth interval) and then returns to its original rest shape during recovery (i.e., at the forty-eighth interval). The ECG also may exhibit a U wave, which is a small deflection following the T wave and related to altered repolarization of the heart. Collections of beats may be chosen based on periods of uniform wave components, such as periods having normal or inverted T waves.

Figure 3C:
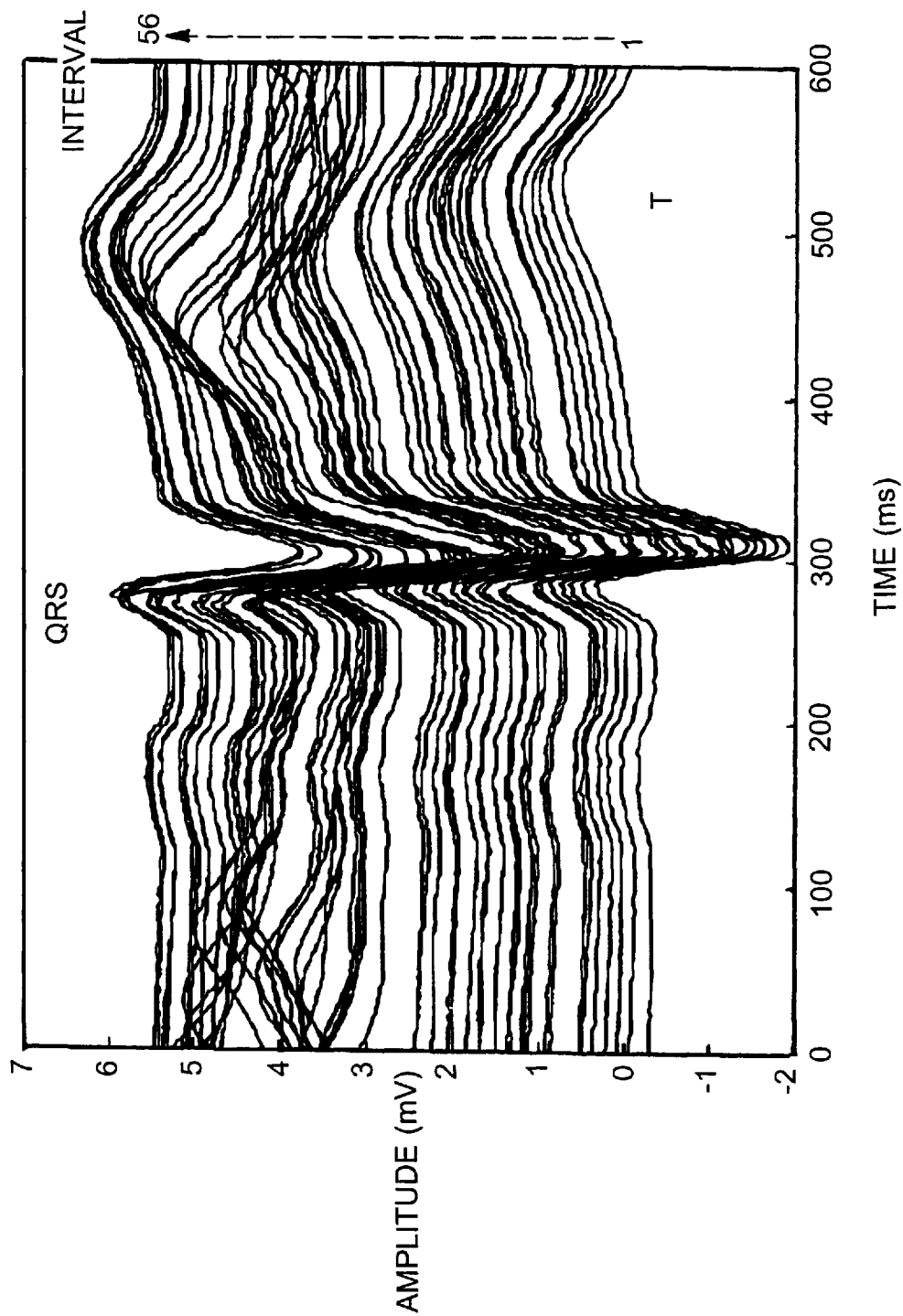

The time from the start of the QRS complex to the end of the T wave, known as the QT time, is known to shorten with increasing heart rate, and is expected to be altered in the presence of myocardial ischemia. As shown in FIG. 3C, a progressive change in QT time is apparent during exercise. During recovery, the QT time returns towards the rest state. Selecting beats in intervals with approximately equal QT times is a useful way to identify QT changes in the ECG associated with exercise. Collections of beats may be chosen based on periods of uniform wave timing, such as periods of approximately equal QT times.

Figure 3D:
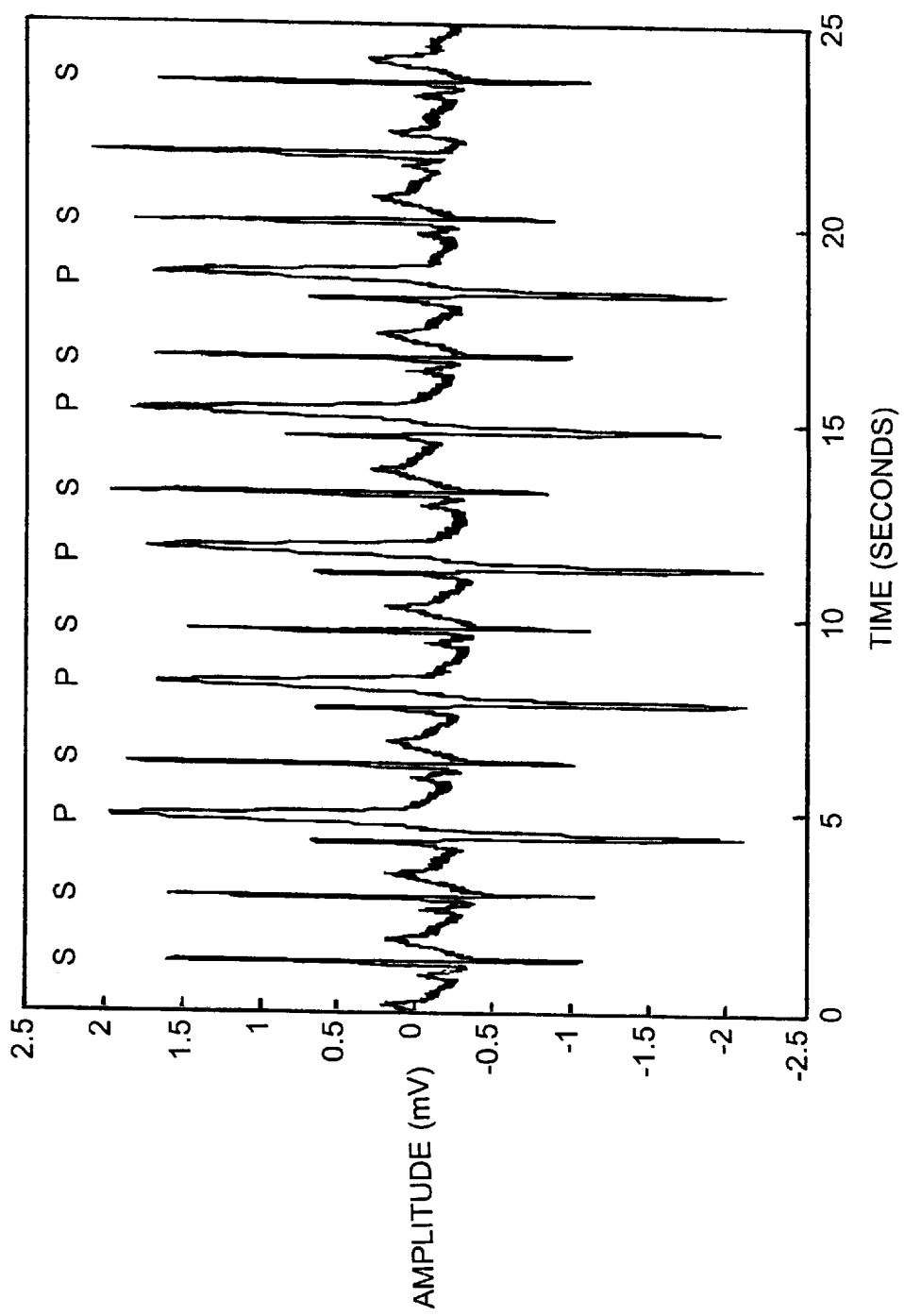

The subensemble also may be selected based on patterns of beat-to-beat variation. For example, as discussed below, when the enhanced ECG beats are to be used in detecting alternans, one subensemble may include even-numbered beats while the other ensemble includes odd-numbered beats. Subensembles also may be selected based on other rhythms, such as N-geminy rhythms, that may occur during stress testing. Referring to FIG. 3D, the ECG may show bi-geminy, a repetitive sequence of one normal beat ("S") followed by an abnormal beat ("P"). The collection of beats may be chosen from the normal beats during a period of N-geminy.

The subensemble may be selected to include only a particular type of beat. The type of beat may be defined by rhythm. For example, all normal sinus rhythm beats may be included in the subensemble average. Alternatively, the type of beat may be defined by arrhythmia context. For example, all normal sinus rhythm beats preceding an ectopic beat may be included in the subensemble. In yet another variation, the subensemble may include only beats with a particular time relationship to each other (e.g., even or odd numbered beats in a sequence of beats).

Referring again to FIG. 2, the controller 120 then produces a representative beat for each subensemble (step 220). In general, the representative beat is a low-noise beat obtained by combining the subensemble of beats. Techniques for combining beats to form a representative beat include median beat formation and subensemble averaging.

During a physiologic stress test, and in other situations in which changes in ECG waveforms are estimated, a sequence of subensembles may be formed by including beats within distinct stages of the stress test. For each subensemble, the subensemble average of R beats selected after preprocessing may be expressed as:

$$\bar{x}_R(t) = \sum_{i=1}^{R} x_i(t)/R$$
$$= s(t) + \sum_{i=1}^{R} n_i(t)/R$$
$$= s(t) + \bar{n}(t)/\sqrt{R},$$

where s(t) is the repetitive, deterministic cardiac signal, n(t) is the noise content of a typical record in the subensemble, i is an index into the array of beats, and $n_i(t)$ is the noise content of a particular beat.

Next, the controller 120 produces a two-dimensional representation of the representative beat (e.g., the subensemble average) for a subensemble (step 225). This may be done, for example, by using a short time Fourier transform ("STFT") to estimate the time-frequency representation ("TFR") of the subensemble average. The TFR is a two-dimensional representation that expresses the ECG waveform as a numerically complex quantity with one dimension being time and the other dimension being frequency. See P. Lander et al., "Spectro-temporal analysis of ventricular late potentials", J. Electrocardiol. 23:95–108, (1990), which is incorporated by reference.

Figure 4:
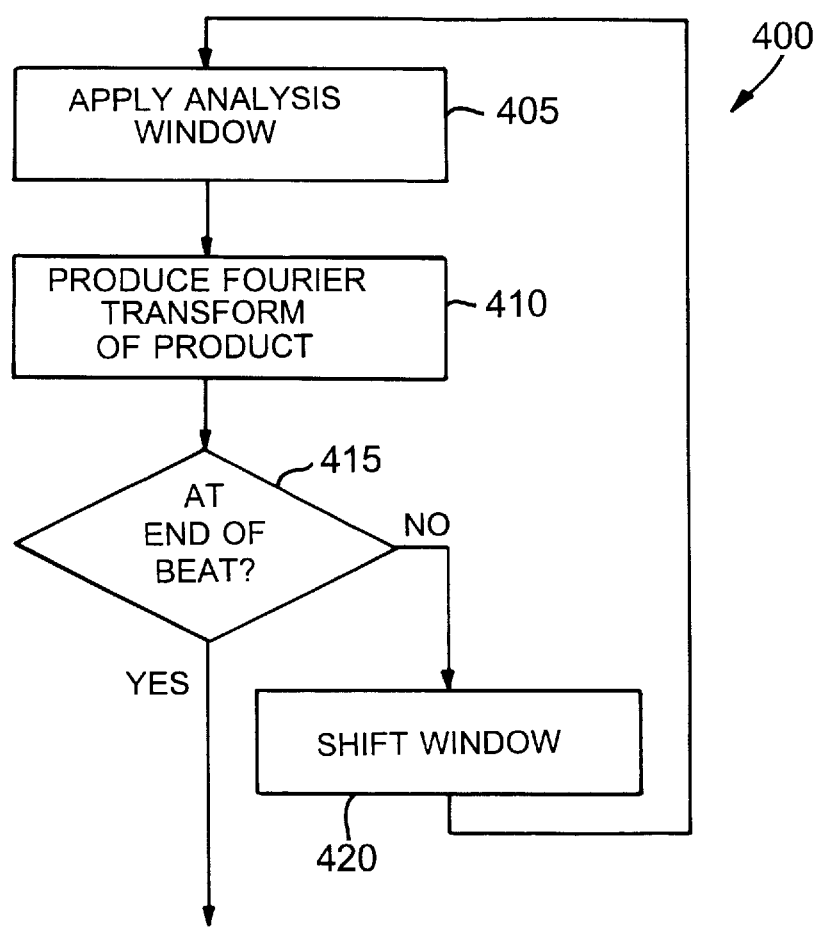
FIG. 4 is a flowchart of a procedure for generating a two-dimensional representation of an ECG beat.

The TFR for a subensemble average may be generated according to the procedure 400 illustrated in FIG. 4. First, an analysis window of fixed or variable duration is applied at the start of the subensemble-averaged beat (step 405). Next, a short-time Fourier transform is applied to the product of the ECG waveform and the analysis window (step 410) to produce the first spectral slice of the TFR. If the window is not at the end of the subensemble-averaged beat (step 415), the window is shifted a fixed amount in time (step 420) and reapplied (step 405). In this manner, successive spectral slices are computed and stored in an array defining the linear TFR (TFRL) of the subensemble-averaged beat. The linear TFR (TFRL) may be expressed mathematically as:

$$\bar{x}(t,f) = TFR_L[\bar{x}(t)]$$
$$= STFT[\bar{x}(t)] = \int \bar{x}(\tau)w(\tau - t)e^{-j2\pi f\tau}d\tau$$

where w(t) is the analysis window. In one implementation, the analysis window is a Hanning function having a duration of 20 milliseconds, and the time increment between successive window shifts is 10 milliseconds (i.e., exactly half the window duration). In general, the analysis window may be any function that is approximately symmetrical in time with respect to its center. The TFR is a linear TFR, as indicated by the subscript L, and has a real and imaginary part.

The two-dimensional representation of the ECG also may be produced using a wavelet transform. The wavelet transform uses a decaying complex sinusoid (a "wavelet") in place of the regular complex sinusoid of the Fourier transform. The wavelet transform offers a trade off between the relative resolution in time and frequency directions (e.g., the time resolution may be increased by decreasing the frequency resolution). The overall time-frequency resolution is unchanged, however, since it is defined by the uncertainty principle.

The wavelet transform uses a basis set of damped sinusoid-like "wavelets". Each wavelet has complementary resolution in the time and frequency directions. A wavelet that has a short duration has good time resolution and correspondingly poor frequency resolution. A wavelet with long duration averages data over time but has correspondingly better frequency resolution. Wavelet analysis is capable of decomposing the ECG signal adaptively, with multiple resolutions in time and frequency. The continuous wavelet transform (CWT) is defined as the integration of the ECG, x(t), multiplied by scaled, shifted versions of the wavelet function $\gamma(t)$:

$$C(a,k) = \int_{-\infty}^{\infty} x(t)\gamma(a,k,t)dt,$$

where the wavelet coefficients are a function of scale, a, and position, k. The original ECG signal is decomposed by multiplying each coefficient by an appropriately scaled and shifted wavelet. Scaling a wavelet means stretching it in time ($\gamma(t/a)$). By varying a, the desired frequency range can be swept. Shifting means delaying ($\gamma(t-k)$). By varying k, the desired time interval can be swept. The function C(a,k) is a two-dimensional time-scale representation. It is equivalent to the time-frequency representation except that it offers differences in time-frequency resolution, depending on the time interval or bandwidth of each ECG component.

The two-dimensional representation of the ECG also may be produced using the Wigner-Ville transform, which offers a high degree of flexibility for choosing a two-dimensional smoothing function. An advantage of the Wigner-Ville distribution is that is has theoretically optimal time-frequency resolution. This means that the Wigner-Ville distribution can obtain the best discrimination between signal and noise in the time-frequency plane. To achieve this best discrimination, it is necessary to smooth the Wigner-Ville distribution to reduce interference components. Interference components are cross-products between the signal and noise components which are not meaningful. The short-time Fourier transform of an ECG can be modelled mathematically as the Wigner-Ville distribution of the ECG after smoothing with the Wigner-Ville distribution of the analyzing window. The Wigner-Ville distribution offers the greatest degree of flexibility in choosing a two-dimensional smoothing function, a step critical in the enhancement of the two-dimensional representations.

The Wigner-Ville distribution, WD, is a time-frequency representation expressed mathematically as:

$$WD[x(t)] = \int x(t + \tau/2)x^*(t - \tau/2)e^{-j2\pi f\tau}d\tau,$$

where x(t) is the ECG signal and x*(t) is the complex conjugate of the ECG signal.

The two-dimensional representation also may be produced by projecting the ECG waveform onto a specific basis set designed from ECG waveforms. This approach has the advantage that components of the ECG can be processed separately in the plane of the two-dimensional representation. With the short-time Fourier transform, the basis set of the transformation includes orthogonal complex sinusoids. Although its properties are well understood, this basis set does not fit the ECG particularly well. An improved basis set could be a damped complex sinusoid, which would model the QRS complex more closely. A potentially superior alternative is to use an ECG waveform itself as the wavelet from which to construct the basis set. Such a basis set could be obtained from a single, typical ECG waveform. As an alternative, a dictionary of ECG waveforms could be used, with the ECG waveform in the dictionary that is closest to the ECG under study being selected. Another alternative is to use a composite ECG waveform that is an average of typical ECG waveforms encountered.

Referring again to FIG. 2, in addition to determining the linear TFR (TFR$_L$) of the subensemble average (step 225), the quadratic TFR (TFR$_L$) is determined (step 230) to express the subensemble average as an energetic distribution in the time-frequency domain. The quadratic form of the STFT may be expressed as:

$$\bar{X}(t,f) = TFR_Q[\bar{X}(t)] = |STFT[\bar{X}(t)]|^2.$$

Quadratic TFRs (TFR$_Q$) also are determined in the same way for each of the R beats in the subensemble (step 235). The R TFR$_Q$s then are averaged (step 240). When the STFT is employed, the average may be expressed as:

$$\overline{X_i(t,f)} = \sum_{i=1}^{R} TFR_Q[x_i(t)]/R.$$

The quadratic TFRs then are used in generating a two-dimensional filter function. The quadratic TFR of the subensemble average may be expressed ideally as:

$$\bar{X}(t,f) = S(t,f) + \bar{N}(t,f)/R$$

and the average of the quadratic TFRs for the subensemble may be expressed ideally as:

$$\overline{X_i(t,f)} = S(t,f) + \bar{N}(t,f)$$

where S(t,f) and $\bar{N}$(t,f) are the cardiac signal and the averaged noise energies of the R-beat subensemble, respectively. In the time-frequency plane, the averages may be represented more realistically as:

$$\bar{X}(t,f) = S(t,f) + COV[S(t,f), N_{\bar{x}}(t,f)]IF[\bar{X}(t,f)]$$

and $$\overline{X_i(t,f)} = S(t,f) + \overline{N_i(t,f)} + \sum_{i=1}^{R} COV[S(t,f), \overline{N_i(t,f)}]/R + \sum_{i=1}^{R} IF[X_i(t,f)]/R$$

where N$_{\bar{x}}$(t,f) is the noise power of the subensemble average, N$_i$(t,f) is the noise power of beat i, and $\overline{N_i(t,f)}$ is the average noise power of the ensemble, and COV[ ] and IF[ ] represent covariance and interference terms, respectively.

To account for this difference, the two-dimensional representations, $\bar{X}$(t,f) and $\overline{X_i(t,f)}$ are enhanced to approximate their ideal values (steps 245, 250). This may be achieved by applying a time-frequency smoothing, or kernel, function to attenuate the variance, covariance, and interference terms. The specification of this two-dimensional smoothing function is made in the time-frequency plane. The spectrograms, $\bar{X}$(t,f) and $\overline{X_i(t,f)}$, are first considered as bilinear TFRs belonging to the class of filtered Wigner distributions. This can be seen in the relation:

$$|STFT[x(t)]|^2 = WD[x(t)] * WD[w(-t)].$$

That is, the spectrogram can be thought of as the convolution of the Wigner distributions (WD) of the ECG waveform, x(t), and the time-reversed STFT analyzing window, w(−t). The WD of the ECG is given by:

$$WD[x(t)] = \int x(t+\tau/2)x^*(t-\tau/2)e^{j2\pi f\tau}d\tau.$$

The analyzing window itself significantly smoothes the Wigner distribution of the ECG, an action which happens implicitly in the computation of the STFT.

The spectrogram is further smoothed by convolution with a two-dimensional lowpass filter that maximizes reduction of the variance, covariance, and interference terms. Simultaneously, the two-dimensional lowpass filter maximizes signal concentration in time-frequency and minimizes bias in the filter coefficients. The smoothed TFR of the ECG, $X^S(t,f)$, can be formulated as:

$$X^S = (t,f) = WD[\bar{x}(t)] * WD[w(-t)] * WD[\gamma(t)]$$

where $WD[\gamma(t)]$ is the smoothing TFR and $\gamma(t)$ is the smoothing function in the time domain. Variance and covariance terms are not expected to be coherent in the time direction, i.e. between successive spectral slices. Interference terms in the spectrogram are limited to a region of the TFR determined by the analyzing window. This region bounds the width in time of the smoothing TFR. The spectrogram has a mainlobe/sidelobe structure set by its analyzing window, w(t). The time-width of the smoothing TFR, $WD[\gamma(t)]$, depends on the mainlobe width and sidelobe level, the corresponding definition of signal concentration, and the variance reduction required. High concentration of signal energy and high variance reduction require small and large time-frequency areas, respectively, for the TFR smoothing function. Hence a trade-off is necessary. In general, the shape of the TFR smoothing function should not be square, but instead is longer in frequency, given the one-dimensional distribution of variance and covariance terms.

The TFR smoothing function may be a two-dimensional Gaussian produced by computing the Wigner-Ville distribution of the time domain function given by:

$$\gamma(t) = e^{-\alpha t}$$

with a value of α=30. This function has a practically minimum time-bandwidth product, maximizing signal concentration in time-frequency. The function is monotonic in time-frequency, which allows it to be stretched or tapered in any direction, permitting an unequal degree of smoothing in the time and frequency directions. There is a further advantage to the monotonicity of the function. A monotonic smoothing function avoids the possibility of constructive interference between the sidelobes of the analyzing window and the smoothing function.

The smoothing TFR also may be a priori designed from a set of representative electrocardiogram waveforms or their principal components. This permits enhancement of the two-dimensional electrocardiogram representations using the known, typical characteristics of the electrocardiogram waveform.

A time-frequency kernel also may be employed as the smoothing function. The time-frequency kernel is a two-dimensional smoothing function that maximizes the ratio between the signal and interference components of the ECG in the time-frequency plane. An idealized ECG signal itself can be used as the kernel. Such a signal could be obtained by selecting a single, typical ECG waveform. This waveform is then transformed to the time-frequency plane and its time-frequency distribution used as the kernel. A dictionary of ECG waveforms could alternatively be used, with the selection of the kernel being the closest ECG waveform in the dictionary to the ECG under study.

Similarly, an adaptive, signal dependent kernel may be obtained directly from the two-dimensional representation of the ECG using a signal-dependent kernel estimation procedure. This permits the degree of smoothing to be selected in a data-adaptive manner. This is a powerful approach to optimizing the enhancement of the two-dimensional electrocardiogram representations. It operates by designing a radially Gaussian function to maximize the ratio between actual signal components and interfering components.

Next, a two-dimensional filter is generated using the enhanced TFRs (step 255). This may involve arithmetically combining the smoothed TFRs to produce h(t,f), a time frequency weighting function that may be a time-frequency plane version of the Wiener weighting function, given by:

$$h(t,f) = S(t,f)/(S(t,f) + \bar{N}(t,f)/R).$$

Figure 5A:
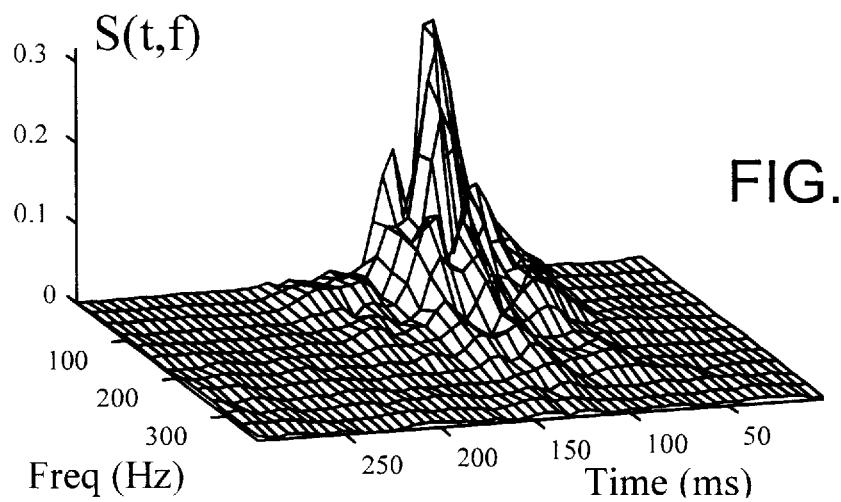
FIGS. 5A–5C illustrating processing of an ECG signal.
Figure 5B:
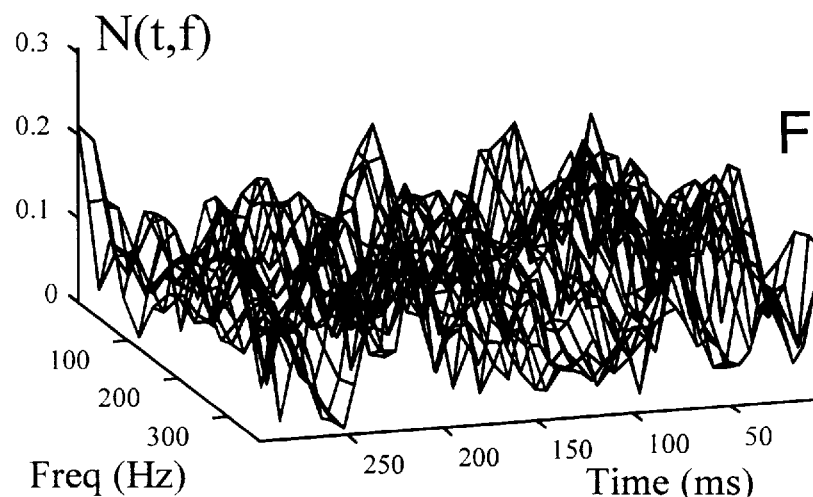
Figure 5C:
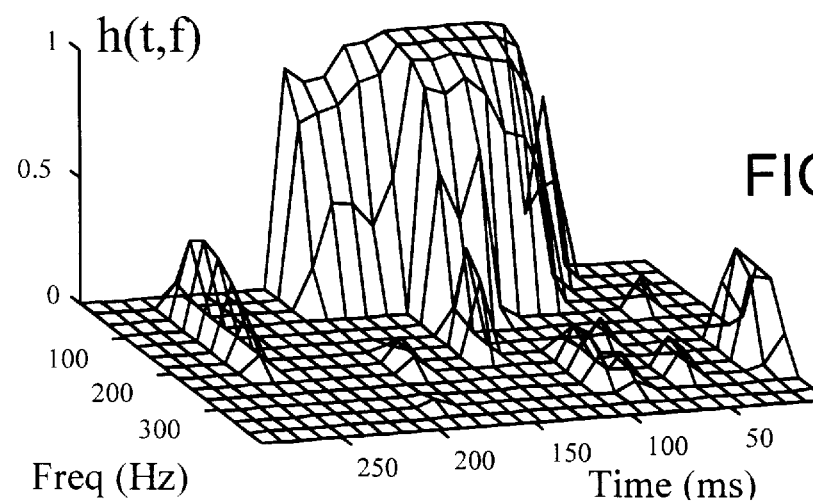

This filter is applicable to an R-beat subensemble average. R is the number of beats in the subensemble average to be filtered, and, in general, can assume any integer value. The filter is applicable to single beats when R equals one. The values of h(t,f) may range from zero to one, with values of h(t,f) outside the range zero to one being clipped to the appropriate one of these values. FIG. 5A shows an example of the estimated quantity, S(t,f), after smoothing. FIG. 5B shows an example of the ensemble noise, $\bar{N}(t,f)$, after smoothing. FIG. 5C shows the filter function computed from S(t,f) and $\bar{N}(t,f)$.

The time-frequency weighting function is tapered in the frequency direction using a lowpass function. The function is a unity transfer function to 200 Hz, then a cosine taper reaching zero at 500 Hz, with a −3 dB value at 250 Hz. After tapering, h(t,f) is lightly smoothed to remove spikes or holes (isolated zeros). The tapered and smoothed weighting function is denoted by $h^s(t,f)$. This is important since impulsive changes in h(t,f) would act as brickwall filter elements, with subsequent phase distortion effects.

The filter then is applied to the linear TFR of the subensemble average (step 260). For example, the weighting function TFR may be applied multiplicatively to the linear TFR of the subensemble average (i.e., the complex STFT) to yield a TFR of the estimated signal:

$$\hat{s}(t,f) = \bar{x}(t,f)h(t,f).$$

Finally, the TFPW filtered signal estimate is obtained by inverse transforming the filtered TFR($\hat{s}(t,f)$) to the time domain (step 265):

$$\hat{s}(t) = STFT^{-1}[\hat{s}(t,f)].$$

The STFT analyzing window is a cosinusoidal-class window with exactly 50% overlap. Reconstruction of $\hat{s}(t)$ is therefore achieved by summation of each inverse transformed spectral slice after appropriate time shifting.

The analysis window may be matched to the time-frequency structure of the ECG and be of variable duration. In this case, after inverse transformation of each spectral slice, each window of data is shifted by the appropriate amount to move the windows of data to their original position in the time domain. Windows of variable duration may not overlap by exactly 50%. To achieve an unbiased signal estimate, each sample in ŝ(t) is multiplied by a compensating value such that each time sample of the filtered signal has an approximate weight of 1.0 relative to all other time samples of the filtered signal. Occasionally, ŝ(t) exhibits small spikes exactly at the location of the edges of the analyzing window. This is due to the prior enhancement of the two-dimensional representations by smoothing. These transients are automatically detected, and where necessary, removed by application of a 5-ms wide median filter.

Figure 6:
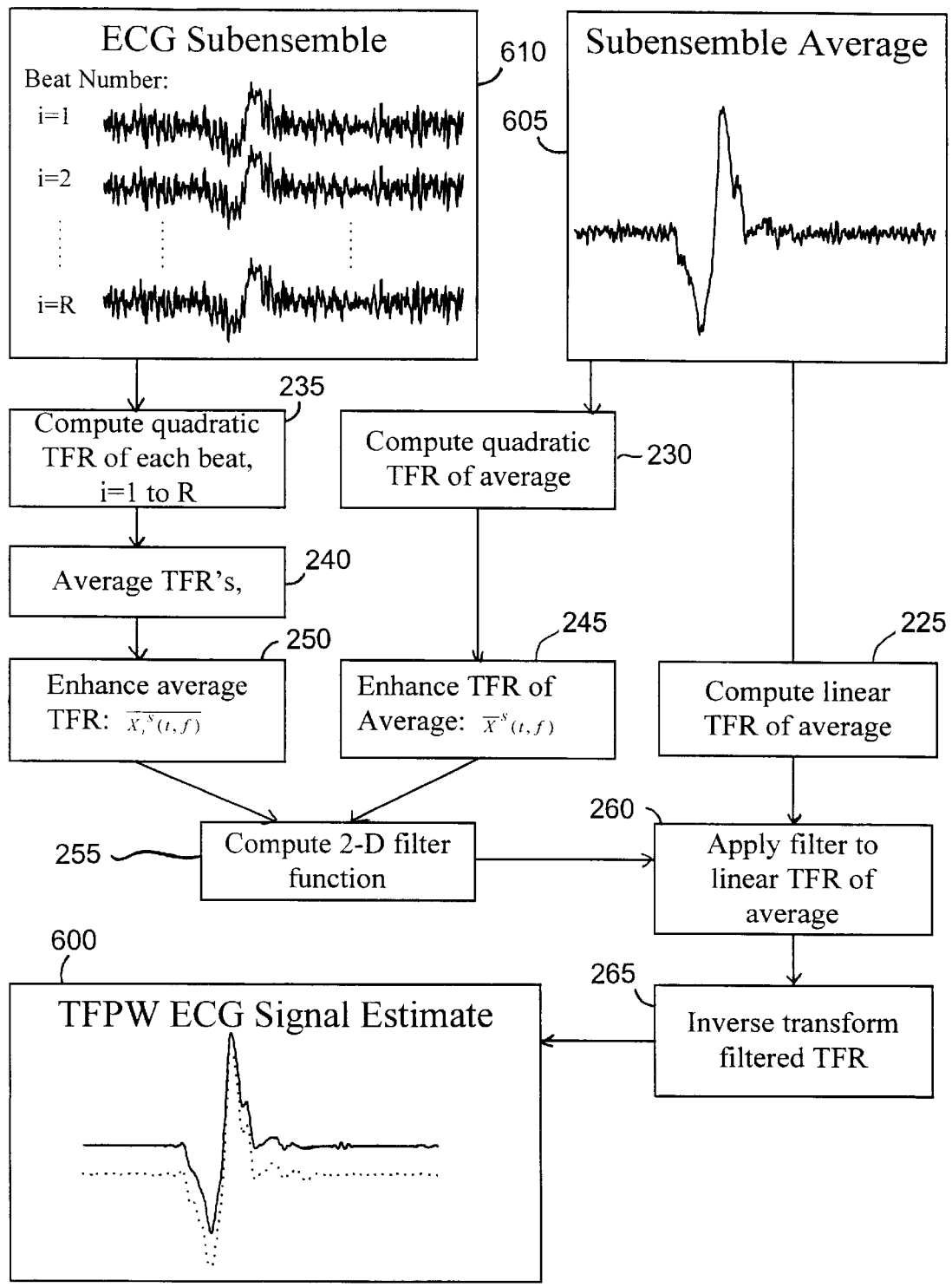
FIG. 6 illustrates the procedure of FIG. 2.

FIG. 6 illustrates generation of an enhanced beat 600 from a representative beat 605 generated for a subensemble 610 according to the procedure 200 of FIG. 2. As shown in FIG. 6, the representative beat 605 has substantially reduced noise relative to the individual beats of the subensemble 610. The enhanced beat 600 includes further reductions in noise relative to the representative beat 605.

Figure 7:
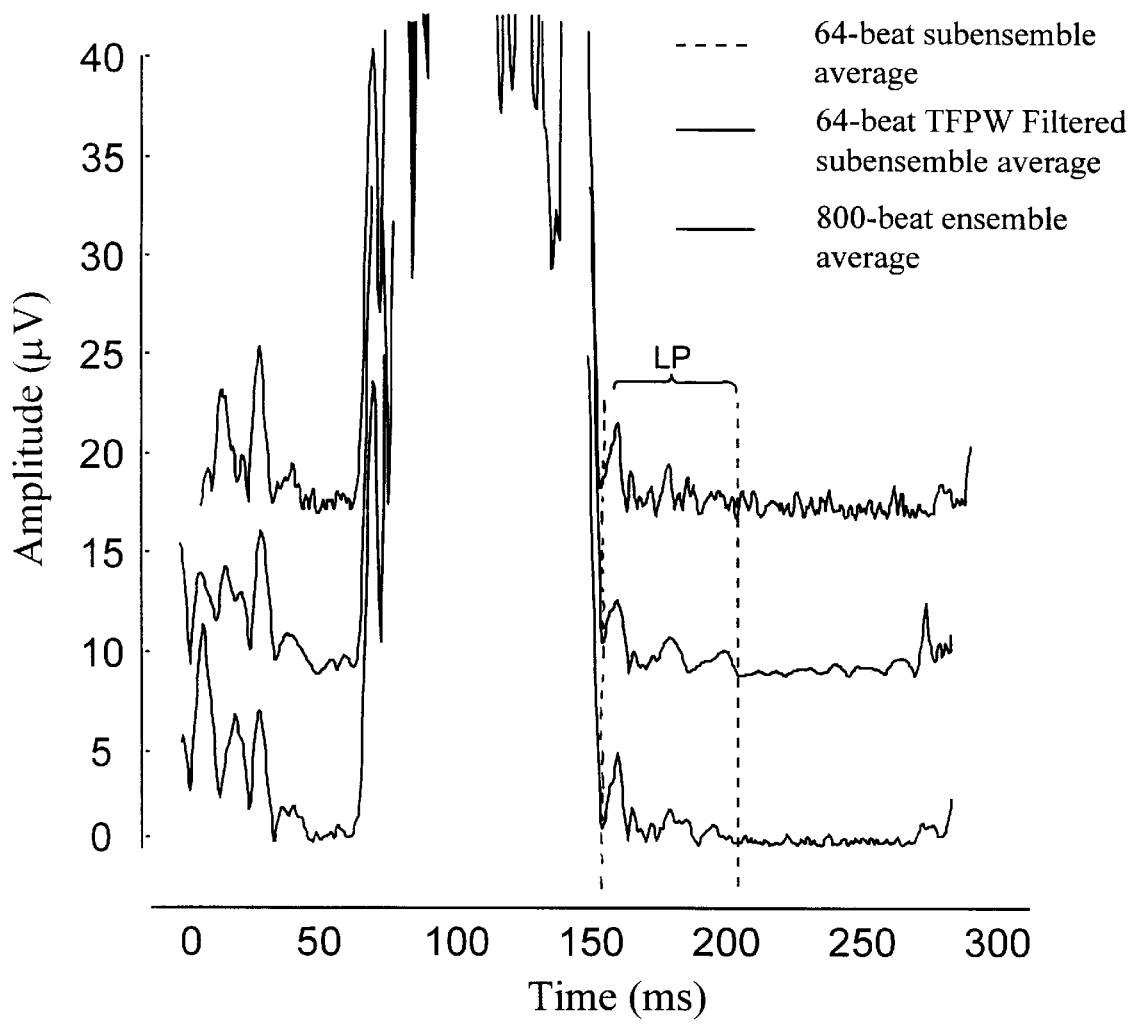
FIG. 7 illustrates results obtained by the procedure of FIG. 2.

FIG. 7 illustrates the application of the TFPW filter to an electrocardiogram subensemble average. All waveforms are the vector magnitude of three resultant orthogonal leads. The top trace shows the conventional 64-beat subensemble average without TFPW filtering. The part of the waveform labeled LP is ventricular late potential activity. The vertical dashed line shows the endpoint of this activity, which is indiscernible in the 64-beat subensemble average. The middle trace shows the same 64-beat subensemble average after application of the TFPW filter. The signal-to-noise ratio of the late potentials is considerably improved and their endpoint is now well-defined. The bottom trace shows the 800-beat ensemble average waveform, with a correspondingly higher signal-to-noise ratio. The waveform is comparable to the TFPW filtered subensemble average which uses 64 as opposed to 800 beats.

The TFPW filter may be used in a number of applications, such as physiologic stress testing, detection of ECG alternans, generation of localized ECG signals, and patient monitoring. During physiologic stress testing, high levels of noise are present in the ECG. These result from muscle activity and movement artifact and are usually of high enough amplitude to obviate any analysis of ECG small-signals. It is sometimes difficult to perform conventional (ST segment) analysis of the ECG in particularly high noise situations. Stress testing uses timed stages, typically including a control period before stress, four or more stages of progressively increased stress, a recovery period immediately after stress, and a subsequent later period when the effects of stress are assumed gone. Subensembles of normal sinus rhythm beats are selected in each stage. The TFPW filter is computed and applied to each subensemble average. The TFPW filter consequently has several uses during stress testing. These include detection and quantification of subclinical ST segment changes; and subtle changes in the QRS and T waves, none of which are visible in the conventional ECG. Elucidation of such ECG changes will be useful in identifying normal and pathological cardiac states, such as myocardial ischemia, myocarditis and myocardial infarction.

ECG alternans is a pattern of alternating changes in ECG shape on a beat by beat (i.e., ABAB) basis. Alternans is almost always a subtle phenomenon with the alternating signal strength being in the range of 1–20 $\mu$V. Alternans signals are therefore not visible in either the resting or exercise ECGs. Particularly during exercise stress testing, where noise levels can easily exceed 100 $\mu$V, the TFPW filter will be of great utility in measuring the alternating signal. A subensemble of ECG beats may be formed during each stage of the stress test. The number of beats may be limited by exclusion of beats with extraneous noise, exclusion of beats in periods where the heart rate is atypical, and exclusion of beats where irregular or ectopic beats cause phase resetting of the alternans phenomenon.

The sequence of beats in the subensemble is then divided into even and odd numbered beats. The TFPW filter is computed and applied independently to each subensemble average. The alternans signal is then computed by subtraction of either subensemble from the other. In another approach, the TFPW filter is computed independently for each subensemble. The TFPW filter is then applied to each beat in its respective subensemble. ECG alternans is then computed using the filtered beats.

Figure 8A:
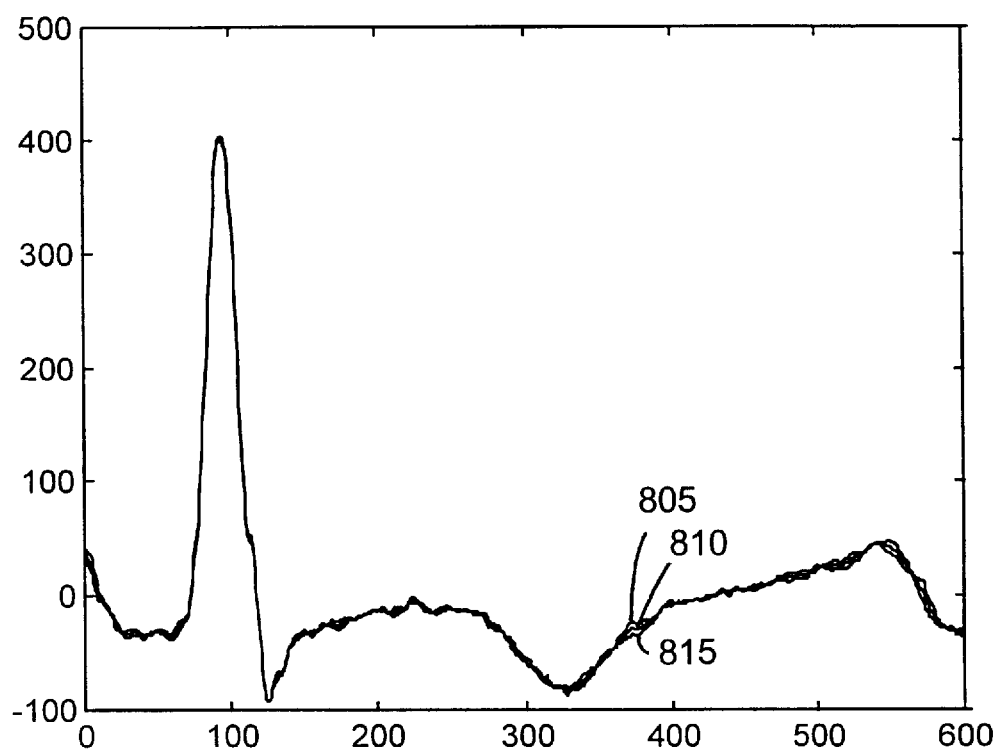
FIGS. 8A–8C are graphs illustrating detection of alternans.
Figure 8B:
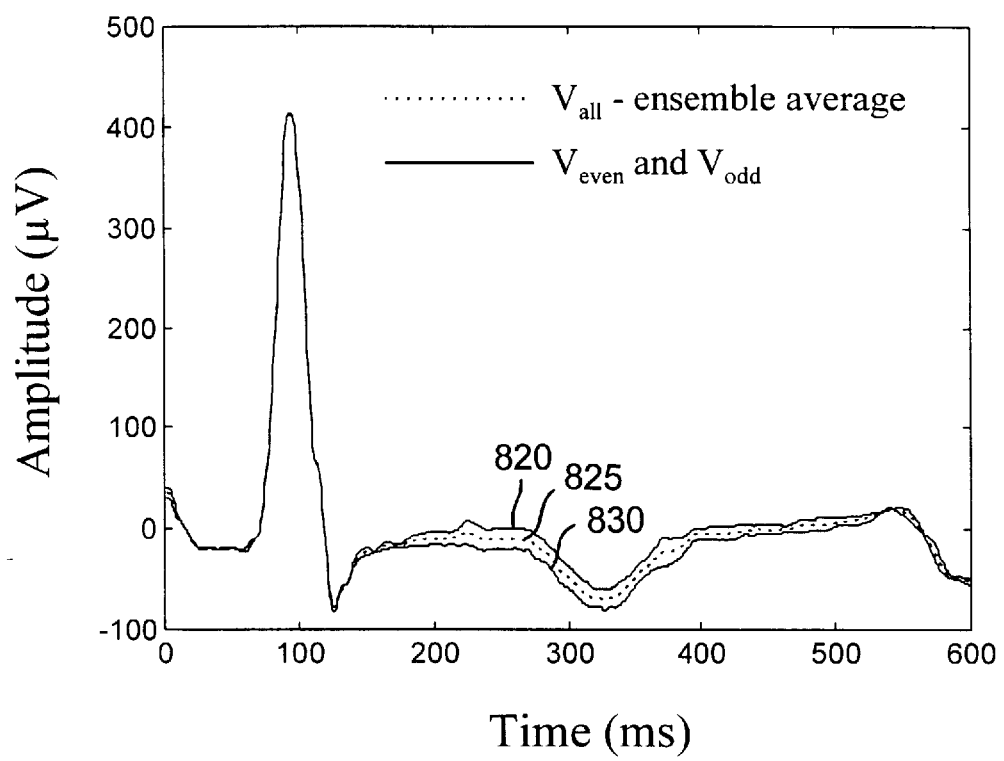
Figure 8C:
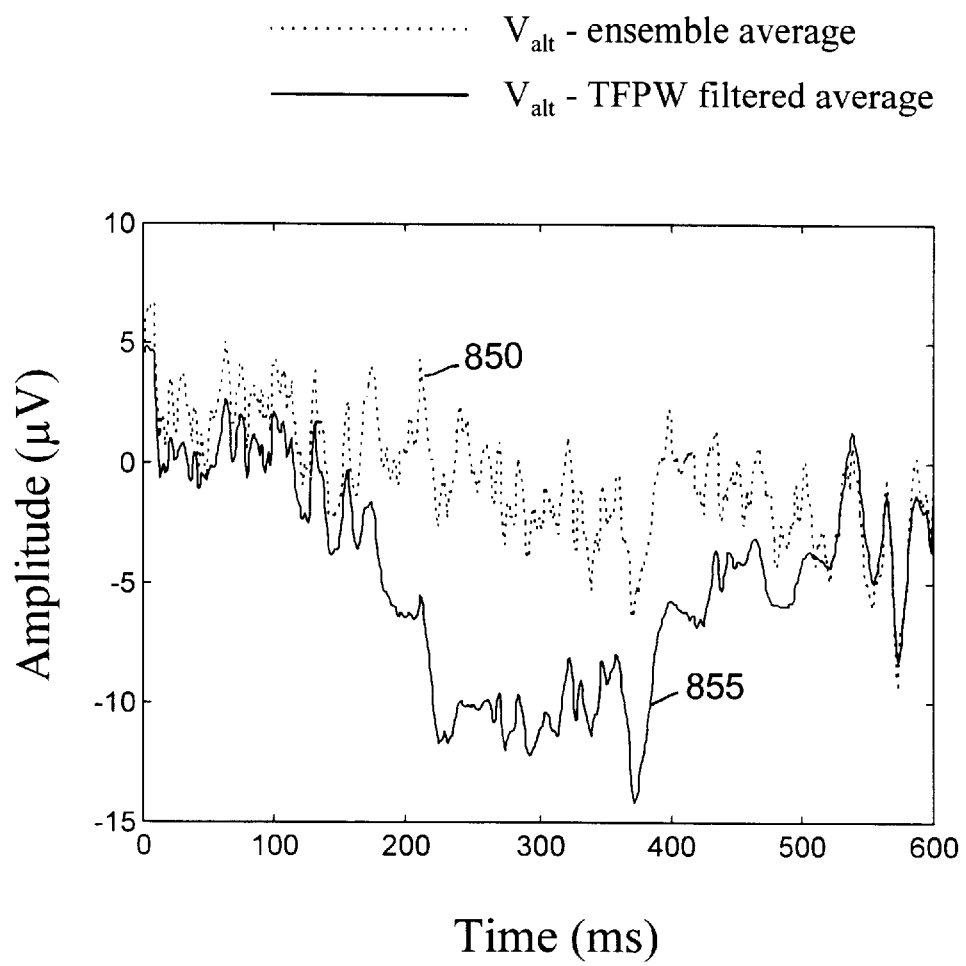

FIG. 8A shows three overlapping traces corresponding to (1) the average of 128 beats (trace 805), (2) the average of the 64 even beats of the 128 beats (trace 810), and (3) the average of the 64 odd beats of the 128 beats (trace 815). As can be seen from FIG. 8A, the difference between the three traces is negligible, and may be attributed to noise. By contrast, FIG. 8B illustrates the same three traces after application of the two-dimensional filtering technique of the invention. As shown in FIG. 8A, there is a distinct difference between the T-wave portions of the average trace 820, the even-beat trace 825, the odd-beat trace 830. FIG. 8C illustrates traces of an alternans waveform (i.e., the difference between the even and odd beats) for the unfiltered signals of FIG. 8A (trace 850) and the filtered signals of FIG. 8B (trace 855). As can be seen from FIG. 8C, the trace 855 includes a significant T-wave portion while the trace 850 does not.

Figure 9:
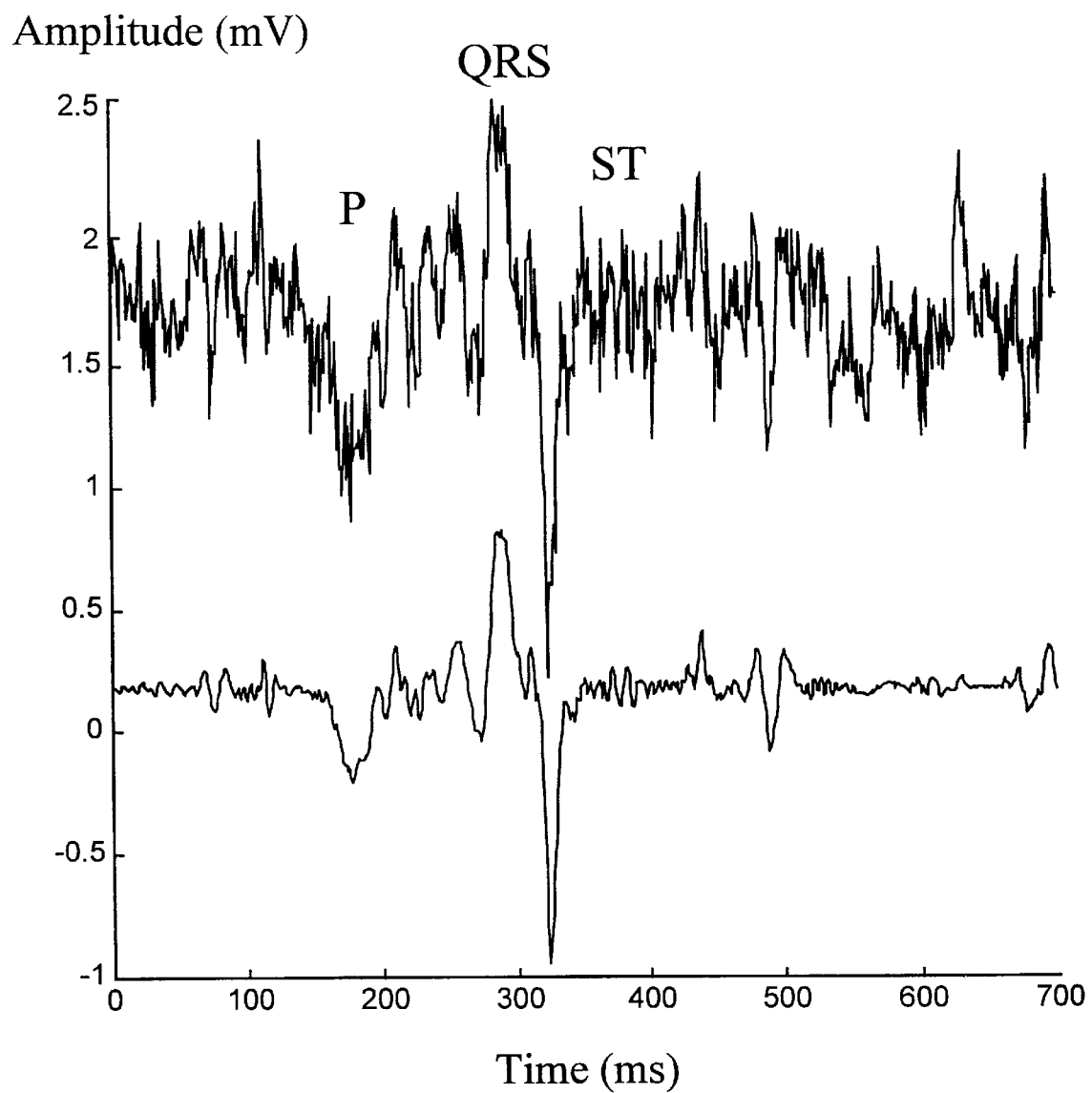
FIG. 9 is a graph illustrating generation of a localized ECG signal.

A localized ECG can be computed using an electrode with multiple segments to obtain an approximation of the Laplacian of the body surface potential distribution. The localized ECG has a lower signal-to-noise ratio than the conventional ECG because of the small signal that results, typically 1–100 $\mu$V. The TFPW filter will be very useful in enhancing the localized ECG signal in a variety of applications, including physiologic stress testing of the heart, ECG monitoring, and detection of suspected myocardial infarction. FIG. 9 illustrates improvements in the localized ECG that may result from application of the TFPW filter. The top trace 905 is a localized ECG signal generated from an average of 300 beats. The bottom trace 910 is a localized ECG signal generated from the same 300 beats after application of the TFPW filter. As can be seen from FIG. 9, noise in the trace 910 is reduced substantially relative to noise in the trace 905.

The TFPW filter will be useful in ECG monitoring applications, including ambulatory monitoring where ECG noise levels can greatly exceed the level of cardiac signals of interest. Example applications include the evolution of ventricular late potentials, intra-QRS signals, ECG alternans signals and ST segment changes. In a preferred embodiment, the TFPW filter will be computed from, and applied to, successive subensembles comprising beats from sequential epochs of one to five minutes duration. The resulting ECG signal trends and changes will be of utility in identifying normal and pathological cardiac states.

The patient's heart may be stressed using a controlled protocol. The protocol may consist either of exercise or of pharmaceutical stress testing. For example, the patient may be exercised using the treadmill 145. Alternatives to the treadmill, such as climbing and bicycle ergometers, also may be used. In general, the stress protocol will have several stages, including control or warm-up stages, stages featuring progressively heavier stress, a relaxation stage, and a recording stage occurring between fifteen minutes and twenty four hours after the test. Recording of ECG signals may take place during any or all of these stages.

Other embodiments are within the scope of the following claims.

What is claimed is:

1. A method for reducing noise from an ECG signal representative of activity of the heart of a patient, the method comprising:

altering a physiologic condition of a patient using non-surgical techniques to stress the heart of the patient;

receiving an ECG signal representative of activity of the heart of the patient whose physiologic condition is altered, the ECG signal including a sequence of beats;

selecting a collection of beats from the ECG signal;

transforming the collection of beats into a multi-dimensional representation; and applying a multi-dimensional filter function to the multi-dimensional representation to enhance a signal-to-noise ratio of the collection of beats.

2. The method of claim 1, wherein:

the step of altering the physiologic condition of the patient comprises instructing the patient to engage in normal physical activity for an extended period, and the step of receiving an ECG signal comprises receiving an ECG signal recorded using an ambulatory monitor.

3. The method of claim 1, wherein the step of altering the physiologic condition of the patient comprises subjecting the patient to physiologic stress testing.

4. The method of claim 1, wherein the step of selecting a collection of beats comprises selecting a collection of beats that occupy a particular time epoch.

5. The method of claim 1, wherein the step of selecting a collection of beats comprises selecting a collection of beats characterized by ECG shape, wave components, or wave timing.

6. The method of claim 1, wherein the step of selecting a collection of beats comprises selecting a collection of beats having a particular contextual relationship to irregular beats.

7. The method of claim 1, wherein the step of selecting a collection of beats comprises selecting a collection of beats based on patterns of beat-to-beat variation.

8. The method of claim 7, wherein the step of selecting the collection of beats comprises selecting the collection of beats based on patterns of beat-to-beat variation including alternating components.

9. The method of claim 7, wherein the step of selecting the collection of beats comprises selecting the collection of beats based on patterns of beat-to-beat variation including N-geminy components.

10. The method of claim 1, wherein the transformation step includes application of a wavelet transform to obtain a multi-dimensional, time-scale representation of the collection of beats.

11. The method of claim 1, wherein the transformation step includes using a numerical basis set derived from an electrocardiogram signal to obtain a multi-dimensional representation.

12. The method of claim 1, wherein the transformation step includes use of a Wigner-Ville distribution to obtain quadratic multi-dimensional representations of the collection of ECG beats.

13. The method of claim 1, further comprising enhancing the multidimensional representation to reduce variance and interference terms by means of convolution with a multi-dimensional function.

14. The method of claim 13, wherein enhancing the multi-dimensional representation includes convolution with a two-dimensional Gaussian function.

15. The method of claim 13, wherein enhancing the multi-dimensional representation includes convolution with a time-frequency kernel derived from an electrocardiogram signal.

16. The method of claim 13, wherein enhancing the multi-dimensional representation includes convolution with an adaptive, signal-dependent kernel.

17. The method of claim 1, wherein transforming the collection of beats into the multi-dimensional representation comprises transforming the collection of beats into a two-dimensional representation.

18. The method of claim 17, wherein applying the multi-dimensional filter comprises applying a two-dimensional filter.

19. The method of claim 1, further comprising generating the multidimensional filter function.

20. The method of claim 19, wherein generating the filter includes incorporation of any beat from the collection of beats being processed in an a posteriori computation of a filtered signal estimate.

21. The method of claim 19, wherein generating the filter includes incorporation of a priori information about the ECG signal.

22. The method of claim 21, wherein the a priori information is derived from beats which are not part of the collection being processed.

23. The method of claim 21, wherein the a priori information is derived from sources other than the ECG recording of the patient being processed.

24. The method of claim 1, wherein the application step includes performing an inverse transformation of the multi-dimensional representation after filtering to obtain a one-dimensional signal estimate.

25. The method of claim 24, wherein performing the inverse transformation comprises performing an inverse wavelet transform.

26. The method of claim 24, wherein performing the inverse transformation comprises performing an inverse Wigner-Ville transformation.

27. The method of claim 1, further comprising generating a measure of alternans from the enhanced collection of beats.

28. The method of claim 1, further comprising generating a localized ECG signal using the enhanced collection of beats.

29. The method of claim 1, further comprising generating a measure of myocardial ischemia using the enhanced collection of beats.

30. The method of claim 1, further comprising generating a localized ECG signal from the received ECG signal, wherein the step of selecting the collection of beats comprises selecting the collection of beats from the localized ECG signal.

31. The method of claim 1, further comprising calculating an average of the collection of beats, wherein the step of transforming comprises transforming the average of the collection of beats into a two-dimensional representation.

32. A method for measuring alternans in an ECG signal, the method comprising:

receiving an ECG signal representative of activity of a heart of a patient, the ECG signal including a sequence of beats;

selecting a collection of beats from the ECG signal;

transforming the collection of beats into a multi-dimensional representation;

applying a multi-dimensional filter function to the multi-dimensional representation to enhance a signal-to-noise ratio of the collection of beats; and generating a measure of alternans from the enhanced collection of beats.

33. A method for generating a localized ECG signal, the method comprising:

receiving an ECG signal representative of activity of a heart of a patient, the ECG signal including a sequence of beats;

selecting a collection of beats from the ECG signal;

transforming the collection of beats into a multi-dimensional representation;

applying a multi-dimensional filter function to the multi-dimensional representation to enhance a signal-to-noise ratio of the collection of beats; and generating a localized ECG signal from the enhanced collection of beats.

34. A method for generating a collection of localized beats, the method comprising:

receiving an ECG signal representative of activity of a heart of a patient, the ECG signal including a sequence of beats;

generating a localized ECG signal from the received ECG signal;

selecting a collection of localized beats from the localized ECG signal;

transforming the collection of localized beats into a multi-dimensional representation; and applying a multi-dimensional filter function to the multi-dimensional representation to enhance a signal-to-noise ratio of the collection of localized beats.

35. A method for measuring an interval in an ECG signal, the method comprising:

receiving an ECG signal representative of activity of a heart of a patient, the ECG signal including a sequence of beats;

selecting a collection of beats from the ECG signal;

transforming the collection of beats into a multi-dimensional representation;

applying a multi-dimensional filter function to the multi-dimensional representation to enhance a signal-to-noise ratio of the collection of beats; and generating a measure of the interval from the enhanced collection of beats.

36. The method of claim 35, wherein generating the measure of the interval comprises generating the measure of a QT interval.

37. The method of claim 36, wherein the ECG signal is received from a first lead, the method further comprising:

repeating the receiving, selecting, transforming, applying and generating steps for ECG signals from additional leads; and comparing the generated measures of intervals for the first and additional leads to determine a measure of QT dispersion.

* * * * *

UNITED STATES PATENT AND TRADEMARK OFFICE
CERTIFICATE OF CORRECTION

PATENT NO. : 5,827,195

DATED : October 27, 1998

INVENTOR(S) : Paul Lander

It is certified that error appears in the above-identified patent and that said Letters Patent is hereby corrected as shown below:

Cover page, [56] References Cited, OTHER PUBLICATIONS, the "Changxiu et al." reference, "tranlation" should be --translation--.

Cover page 3, col. 1, [56] References Cited, OTHER PUBLICATIONS, the "Salerno et al." reference, "R-St-Alternans" should be --R-ST-Alternans--.

Column 1, line 47, "altemans" should be --alternans--.

Column 3, line 50, "altemans" should be --alternans--.

Column 8, line 23, "n(t)" should be --$\bar{n}(t)$--.

Column 8, lines 50 and 51, "(TFRL)" should be --$(TFR_L)$--.

UNITED STATES PATENT AND TRADEMARK OFFICE
CERTIFICATE OF CORRECTION

PATENT NO. : 5,827,195
DATED : October 27, 1998
INVENTOR(S) : Paul Lander

It is certified that error appears in the above-identified patent and that said Letters Patent is hereby corrected as shown below:

Column 10, line 15, "$(TFR_L)$" should be --$(TFR_Q)$--.

Column 10, line 47,
"$\tilde{X}(t,f)=S(t,f)+COV[S(t,f),N_{\tilde{x}}(t,f)]IF[\bar{X}(t,f)]$" should be
--$\tilde{X}(t,f)=S(t,f)+N_{\tilde{x}}(t,f)+COV[S(t,f),N_{\tilde{x}}(t,f)]+IF[\bar{X}(t,f)]$--.

Signed and Sealed this

Twenty-second Day of August, 2000

Attest:

Q. TODD DICKINSON

*Attesting Officer*     *Director of Patents and Trademarks*